US009333029B2

(12) United States Patent
Baldwin et al.

(10) Patent No.: US 9,333,029 B2
(45) Date of Patent: May 10, 2016

(54) METHOD AND DEVICES FOR PERFORMING MINIMALLY INVASIVE SURGERY

(75) Inventors: Dalton D. Baldwin, Loma Linda, CA (US); Gideon Richards, Loma Linda, CA (US)

(73) Assignee: TELEFLEX MEDICAL INCORPORATED, Morrisvile, NC (US)

(*) Notice: Subject to any disclaimer, the term of this patent is extended or adjusted under 35 U.S.C. 154(b) by 796 days.

(21) Appl. No.: 13/528,714

(22) Filed: Jun. 20, 2012

(65) Prior Publication Data

US 2012/0259317 A1 Oct. 11, 2012

Related U.S. Application Data

(62) Division of application No. 12/937,705, filed as application No. PCT/US2010/035312 on May 18, 2010, now Pat. No. 8,225,798.

(60) Provisional application No. 61/179,301, filed on May 18, 2009, provisional application No. 61/230,944, filed on Aug. 3, 2009, provisional application No. 61/240,406, filed on Sep. 8, 2009.

(51) Int. Cl.
*A61B 17/29* (2006.01)
*A61B 18/14* (2006.01)
*A61M 1/00* (2006.01)
*A61B 17/34* (2006.01)
*A61B 18/00* (2006.01)

(52) U.S. Cl.
CPC .............. *A61B 18/1482* (2013.01); *A61B 17/29* (2013.01); *A61M 1/008* (2013.01); *A61B 17/2909* (2013.01); *A61B 17/3423* (2013.01); *A61B 2017/292* (2013.01); *A61B 2017/294* (2013.01); *A61B 2017/2931* (2013.01); *A61B 2017/2936* (2013.01); *A61B 2018/00083* (2013.01); *A61B 2018/00107* (2013.01); *A61B 2018/00595* (2013.01); *A61B 2018/1422* (2013.01)

(58) Field of Classification Search
CPC .............. A61B 17/29; A61B 17/2909; A61B 18/1482; A61B 2017/294; A61B 2017/292; A61B 2017/2931; A61B 2017/2936
See application file for complete search history.

(56) References Cited

U.S. PATENT DOCUMENTS

| | | | |
|---|---|---|---|
| 1,841,968 A | | 8/1924 | Lowry |
| 4,359,052 A | | 11/1982 | Staub |
| 4,846,790 A | | 7/1989 | Hornlein et al. |
| 5,147,357 A | | 9/1992 | Rose et al. |
| 5,308,358 A | * | 5/1994 | Bond et al. ..................... 606/205 |
| 5,314,424 A | * | 5/1994 | Nicholas .......................... 606/41 |
| 5,368,606 A | * | 11/1994 | Marlow et al. ................ 606/170 |
| 5,391,166 A | | 2/1995 | Eggers |
| 5,456,684 A | | 10/1995 | Schmidt et al. |
| 5,531,757 A | | 7/1996 | Kensey et al. |

(Continued)

OTHER PUBLICATIONS

Loma Linda University et al., International Search Report and Written Opinion dated Sep. 23, 2010 issued in related International Patent Application No. PCT/US2010/035312.

*Primary Examiner* — Michael Peffley
(74) *Attorney, Agent, or Firm* — Baker and Hostetler LLP

(57) ABSTRACT

A device for use in performing minimally invasive surgery. A system for performing minimally invasive surgery comprising the device according to the present invention. A method for performing minimally invasive surgery.

10 Claims, 28 Drawing Sheets

(56) References Cited

U.S. PATENT DOCUMENTS

| | | |
|---|---|---|
| 5,868,742 A * | 2/1999 | Manes et al. .................... 606/46 |
| 6,406,470 B1 | 6/2002 | Kierce |
| 6,543,456 B1 | 4/2003 | Freeman |
| 7,083,616 B2 * | 8/2006 | Kawai et al. .................... 606/41 |
| 2003/0216725 A1 | 11/2003 | Woloszko et al. |
| 2004/0243157 A1 | 12/2004 | Connor et al. |
| 2007/0043352 A1 * | 2/2007 | Garrison et al. ................ 606/51 |

* cited by examiner

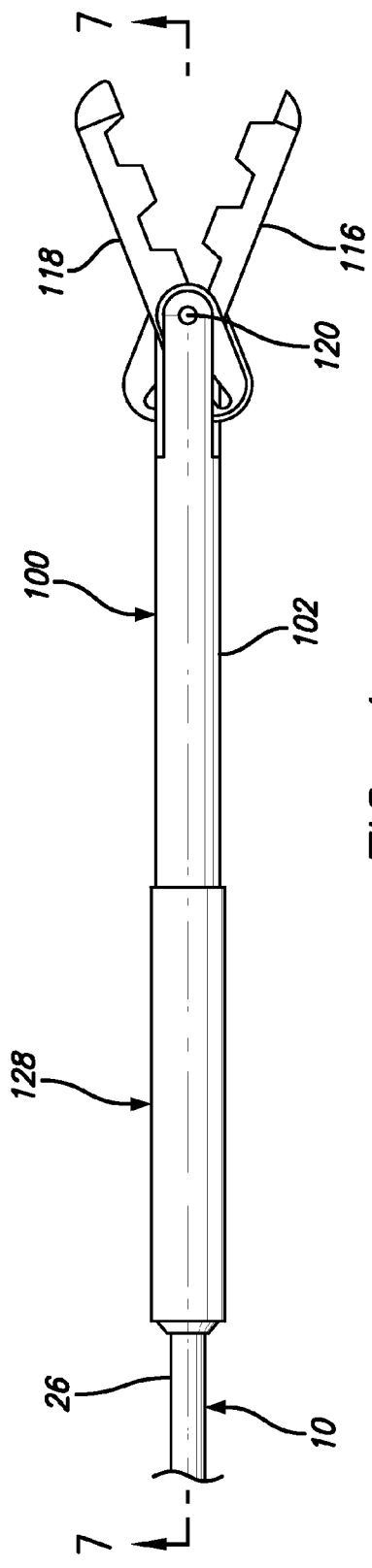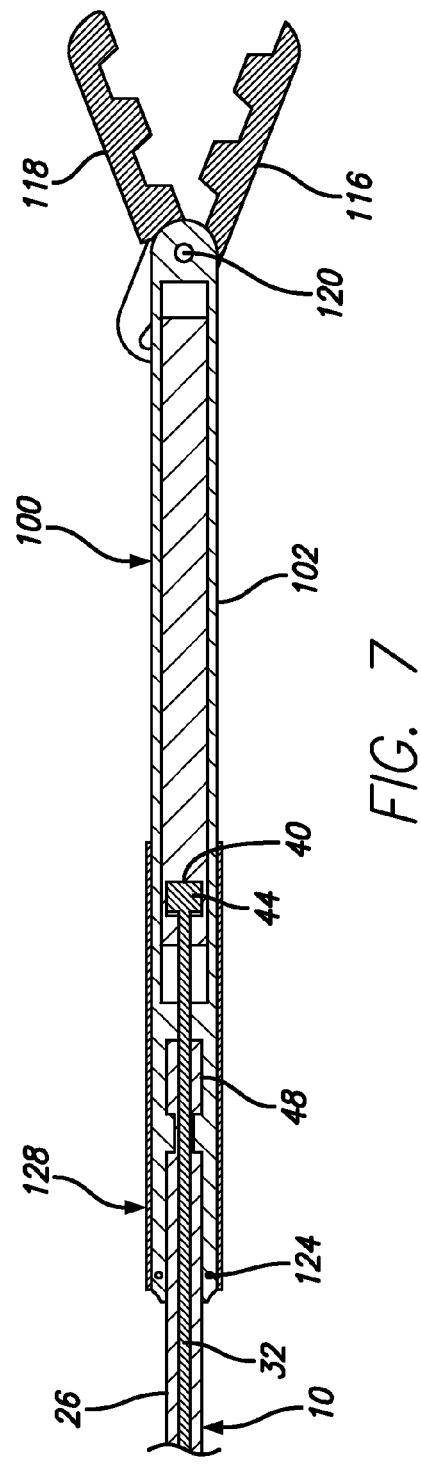

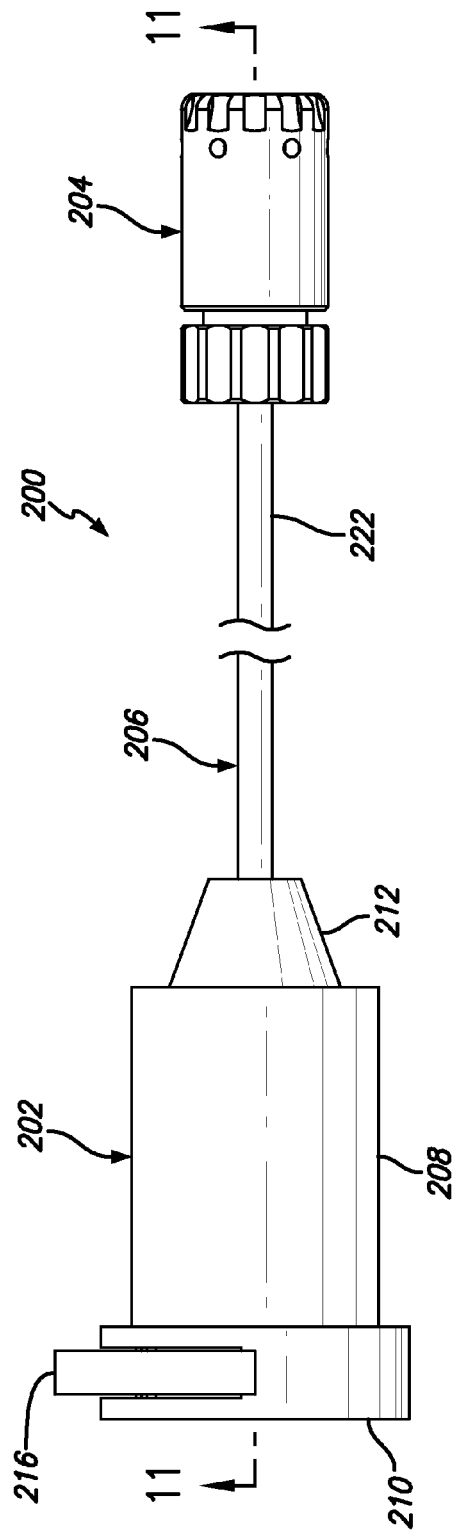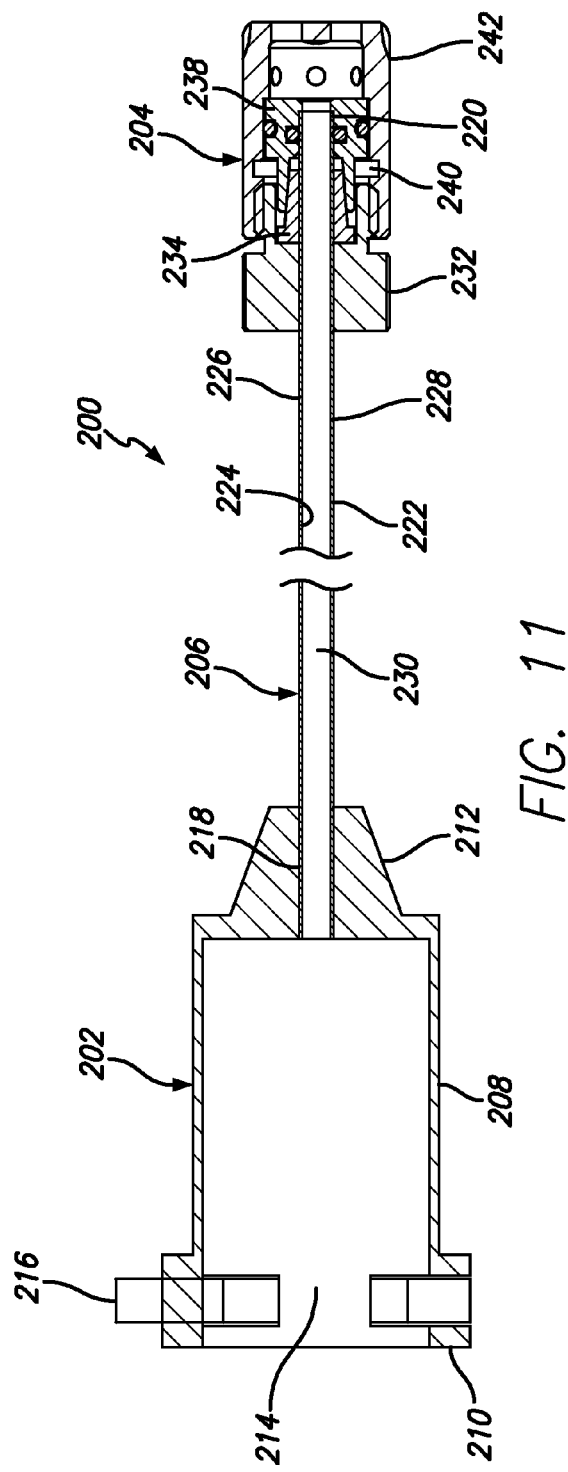
FIG. 10
FIG. 11

METHOD AND DEVICES FOR PERFORMING MINIMALLY INVASIVE SURGERY

CROSS-REFERENCE TO RELATED APPLICATIONS

The present application is a divisional of U.S. patent application Ser. No. 12/937,705, now U.S. Pat. No. 8,225,798, titled: "Method and Devices for Performing Minimally Invasive Burger," filed Oct. 13, 2010 which is a national phase of International Patent Application No. PCT/US2010/035312 titled "Method and Devices for Performing Minimally Invasive Surgery," filed May 18, 2010 which claims the benefit of U.S. Provisional Patent Application No. 61/179,301, titled "Method and Devices for Performing Minimally Invasive Surgery," filed May 18, 2009, U.S. Provisional Patent Application No. 61/230,944, titled "Method and Devices for Performing Minimally Invasive Surgery," filed Aug. 3, 2009 and U.S. Provisional Patent Application No. 61/240,406, titled "Method and Devices for Performing Minimally Invasive Surgery," filed Sep. 8, 2009, the contents of which are incorporated in this disclosure by reference in their entirety.

BACKGROUND

Abdominal surgery is used to treat a variety of diseases and conditions. Techniques for performing abdominal surgery have made major advances during the past 150 years. Originally, surgeons made incisions in the abdominal wall sufficiently large to allow the surgeon to insert both hands into the abdominal cavity to gain easy access to the abdominal organs and to examine the abdominal organs by touch. This surgical method is referred to as "open surgery."

During the 1980's and 1990's, a new form of surgery called "laparoscopic surgery" (standard laparoscopic surgery) was developed that required several smaller incisions of between 5 mm and 20 mm each to create ports for the placement of specialized instruments into the abdominal cavity. Recovery from laparoscopic surgery generally requires less time, is less painful and has fewer complications associated with abdominal wall incisions than does open surgery.

Several forms of laparoscopic surgery have been developed, including "laparoendoscopic single-site surgery" (LESS), where a single incision between 20 mm and 50 mm is made in the crease of the umbilicus and all instruments are introduced into the abdominal cavity through the one incision. The resultant cosmesis is improved in laparoendoscopic single-site surgery (LESS) compared with other forms of laparoscopic surgery because the single scar from laparoendoscopic single-site surgery (LESS) is concealed in the umbilicus, although the single incision is longer in length compared to other forms of laparoscopic surgery. Performing laparoendoscopic single-site surgery (LESS), however, is technically more difficult for the surgeon than other forms of laparoscopic surgery because the surgeon loses the mechanical advantage of triangulating several instruments from different angles that is available with standard laparoscopic surgery.

Another form of laparoscopic surgery called "natural orifice transluminal endoscopic surgery" (NOTES) has been developed where some of the laparoscopic instruments are introduced into the abdominal cavity through natural orifices (the mouth, urethra, anus and vagina), thereby hiding the resultant surgical access scars inside the body. Natural orifice transluminal endoscopic surgery, however, is technically more difficult to perform than standard laparoscopy in both sexes, and is more difficult to perform in men than women because men lack a vaginal canal and thus lack that source of access into the abdominal cavity.

Another form of laparoscopic surgery called "needlescopic surgery" uses devices introduced through ports using 2 mm and 3 mm openings in the abdominal wall. Two millimeter ports leave no visible scar. Three millimeter ports leave small visible scars that are difficult to see even by trained medical personnel. The major limitation on the development of the needlescopic surgery has been the poor functionality of the instruments that fit through the very small ports. Further, instruments that fit through 2 mm ports generally have shafts that are too short to be used in adult sized patients. Additionally, some abdominal procedures require instruments that need larger ports than 3 mm for placement in the abdominal cavity. Because of these limitations, needlescopic surgery has not gained popularity despite potential advantages for cosmesis and patient recovery.

Therefore, there is a need for a new surgical procedure that combines the broad usefulness of standard laparoscopic surgery with its multiple incisions that allow triangulation of instrumentation, but with the improved cosmesis of laparoendoscopic single-site surgery, natural orifice transluminal endoscopic surgery and needlescopic surgery.

SUMMARY

According to one embodiment of the present invention, there is provided a device for use in performing minimally invasive surgery. The device comprises a user interface comprising: a) a proximal portion, an intermediate portion and a distal portion, where the intermediate portion connects the proximal portion to the distal portion; and b) a pushrod, a shaft and a spring; where the distal portion is configured to reversibly mate with a working end; where the proximal portion is configured to allow a user to hold and direct the user interface, and to operate the working end attached to the distal portion of the user interface; where the proximal portion of the user interface comprises a proximal handle and a distal handle joined together by and rotatable around a pivot; where the pushrod comprises a proximal portion of the pushrod and a distal portion of the pushrod; where the proximal portion of the pushrod comprises a proximal end of the proximal portion of the pushrod, and comprises a distal end of the proximal portion of the pushrod; where the proximal end of the proximal portion of the pushrod is linked to the proximal handle, such that movement of the proximal handle around the pivot translates into axial movement of the pushrod; where the distal portion of the pushrod comprises a proximal end of the distal portion of the pushrod, and comprises a distal end of the distal portion of the pushrod; where the distal end of the proximal portion of the pushrod is joined to the proximal end of the distal portion of the pushrod at a junction; where the distal end of the distal portion of the pushrod comprises an expansion for mating with the working end; where the shaft comprises a hollow tubular structure comprising a longitudinal axis and further comprises a proximal portion of the shaft and a distal portion of the shaft; where the shaft surrounds at least part of the distal portion of the pushrod; where the distal portion of the pushrod is axially slidable within the shaft; and where the spring surrounds the proximal end of the distal portion of the pushrod, and the spring is between and abuts the distal end of the proximal portion of the pushrod and the proximal portion of the shaft. In one embodiment, the user interface further comprises a shaft securing pin configured to insert within a recess in the distal handle, thereby securing the shaft from moving relative to the distal handle. In another embodiment, the device further comprises a working end for performing a function during minimally invasive surgery, where the working end is configured to reversibly mate with the distal end of the distal portion of the user interface. In another embodiment, the function is selected from the group consisting of canulating, clip application, cutting, grasping, lighting, recording images, retracting, sealing, suctioning, and viewing images.

According to another embodiment of the present invention, there is provided a device for use in performing minimally invasive surgery. The device comprises a working end for mating with a user interface. The working end has a grasping function, and the working end comprises: a) a head piece comprising a proximal portion of the head piece connected to a distal portion of the head piece; b) a jaw pushrod comprising a proximal portion of the jaw pushrod and a distal end of the jaw pushrod; c) a first jaw and a second jaw connected to the distal end of the jaw pushrod by a jaw pivot; and d) a shaft clamp and one or more than one shaft clamp pins for aligning the shaft clamp with the proximal portion of the head piece; where the distal portion of the head piece is connected to the proximal portion of the jaw pushrod by a jaw pin; where the first jaw and the second jaw approximate and separate from each other in response to axial movement of the jaw pushrod; where the proximal portion of the head piece comprises a recess for mating with the distal portion of the shaft and the distal end of the jaw pushrod; and where the distal portion of the shaft and the distal end of the jaw pushrod are secured to the head piece by placing the shaft clamp onto the proximal portion of the head piece and securing the shaft clamp onto the proximal portion of the head piece by threading a threaded fastener over both the shaft clamp and the proximal portion of the head piece.

According to another embodiment of the present invention, there is provided a device for use in performing minimally invasive surgery. The device comprises a working end for mating with a user interface. The working end has a cutting function and the working end comprises: a) a head piece comprising a proximal portion of the head piece connected to a distal portion of the head piece; b) a blade pushrod comprising a proximal portion of the blade pushrod and a distal end of the blade pushrod; c) a first blade and a second blade connected to the distal end of the blade pushrod by a blade pivot; and d) a shaft clamp and one or more than one shaft clamp pins for aligning the shaft clamp with the proximal portion of the head piece; where the distal portion of the head piece is connected to the proximal portion of the blade pushrod by a blade pin; where the first blade and the second blade approximate and separate from each other in response to axial movement of the blade pushrod; where the proximal portion of the head piece comprises a recess for mating with the distal portion of the shaft and the distal end of the blade pushrod; and where the distal portion of the shaft and the distal end of the blade pushrod are secured to the head piece by placing the shaft clamp onto the proximal portion of the head piece and securing the shaft clamp onto the proximal portion of the head piece by threading a threaded fastener over both the shaft clamp and the proximal portion of the head piece.

According to another embodiment of the present invention, there is provided a device for performing a suction function during minimally invasive surgery. The device comprises a suction connector proximally, a suction head distally and a suction shaft connecting the suction connector to the suction head; where the suction connector comprises a joining piece comprising a proximal end of the joining piece and a distal end of the joining piece, and further comprises a central cavity within the joining piece between the proximal end of the joining piece and the distal end of the joining piece; where the suction connector further comprises a circlip for clamping a source of suction inserted through the proximal end of the joining piece and into central cavity onto the joining piece; where the suction shaft comprises a hollow tubular structure comprising a proximal end of the suction shaft, a distal end of the suction shaft, an intermediate section of the suction shaft connecting the proximal end of the suction shaft to the distal end of the suction shaft, an inner surface of the suction shaft, an outer surface of the suction shaft, a wall of the suction shaft defined between the inner surface of the suction shaft and the outer surface of the suction shaft, a central lumen of the suction shaft defined by the inner surface of the suction shaft, an outer transverse diameter defined by the outer surface of the suction shaft and an inner transverse diameter defined by the inner surface of the suction shaft; where the suction head comprises from proximal to distal a fastener, a shaft clamp, a shaft clamp o-ring, a clamp funnel, a clamp funnel o-ring and a suction tip; where the distal end of the suction shaft passes within the fastener, the shaft clamp, the shaft clamp o-ring, the clamp funnel, and the clamp funnel o-ring and is fixed in position, allowing suction from a source of suction to be delivered to the suction tip, and externally there through; and where the outer transverse diameter of the suction shaft is between 1 mm and 3 mm. In one embodiment, the device further comprises a fine mesh covering the suction tip.

According to another embodiment of the present invention, there is provided a device for performing minimally invasive surgery, where the device is an electrocautery assembly for performing electrocautery. The electrocautery assembly comprises: a) an electrocautery assembly shaft proximally configured to reversibly mate with an electrocautery assembly head distally; where the electrocautery assembly shaft comprises a cylindrical structure comprising a proximal end of the electrocautery assembly shaft, a distal end of the electrocautery assembly shaft, an intermediate section of the electrocautery assembly shaft connecting the proximal end of the electrocautery assembly shaft to the distal end of the electrocautery assembly shaft; b) a central core extending from the proximal end of the electrocautery assembly shaft to the distal end of the electrocautery assembly shaft and an insulation casing surrounding the central core in the intermediate section, where the insulation casing comprises an outer surface of the insulation casing; where the electrocautery assembly shaft further comprises an outer transverse diameter defined by the outer surface of the electrocautery assembly shaft; where the central core comprises material suitable for transmitting an electric charge from the proximal end of the electrocautery assembly shaft to the distal end of the electrocautery assembly shaft; where the insulation casing of the electrocautery assembly shaft comprises material suitable to insulate any electric charge in the central core from the external environment; and where the electrocautery assembly head comprises a proximal end of the electrocautery assembly head, and a distal end of the electrocautery assembly head, and comprises from the proximal end of the electrocautery assembly head to the distal end of the electrocautery assembly head, a proximal section of the electrocautery assembly head connected to an intermediate section of the electrocautery assembly head connected to a distal section of the electrocautery assembly head; where the electrocautery assembly head further comprises an insulation casing of the electrocautery assembly head and a central core of the electrocautery assembly head; where the insulation casing of the electrocautery assembly head surrounds the core in the proximal section of the electrocautery assembly head and the intermediate section of the electrocautery assembly head; where the distal section of the electrocautery assembly head comprises the core of the electrocautery assembly head; where the proximal section of the electrocautery assembly head is a hollow tubular structure defined by the insulation casing and is configured to mate with the distal end of the electrocautery assembly shaft; where the distal end of the electrocautery assembly shaft fits into a matching recess in the intermediate section of the electrocautery assembly head, thereby making electrical contact with the core of the electrocautery assembly head; where the core comprises material suitable for transmitting an electric charge from the distal end of the electrocautery assembly shaft to the distal end of the electrocautery assembly head, and there through to living tissue; where the insulation casing of the electrocautery assembly head comprises material suitable to insulate any electric charge in the core from the external environment; where the distal end of the electrocautery assembly shaft is configured to mate with the proximal section of the electrocautery assembly head; and where the outer transverse diameter of the electrocautery assembly shaft is between 1 mm and 3 mm.

According to another embodiment of the present invention, there is provided a system for performing minimally invasive surgery, where the system comprises one or more than one device according to the present invention. In one embodiment, the system further comprises written or recorded directions for using the one or more than one device. In one embodiment, the system comprises two devices according to the present invention.

According to another embodiment of the present invention, there is provided a method for performing a form of minimally invasive surgery, referred to as "scarless microport augmented restoration of triangulation surgery" (SMART surgery), in a body cavity within a living body, where the body cavity is separated from a space outside of the body by a body wall. The method comprises: a) providing a first device comprising a first part and a second part; b) making two or more than two openings into the body wall, where the two or more than two openings comprise a first opening and a second opening; where the first opening has a maximum transverse dimension that permits introduction of the first part of the first device from the space outside of the body through the first opening and into the body cavity, where the first part of the first device has a maximum external transverse dimension greater than 3 mm; where the second opening has a maximum transverse dimension between 0.1 mm and 3 mm and permits introduction of a second part of the first device from the space outside of the body through the second opening and into the body cavity, where the second part of the first device has a maximum external transverse dimension of between 0.1 mm and 3 mm; c) introducing the second part of the first device from the space outside of the body through the second opening into the body cavity; d) passing the second part of the first device from inside of the body cavity through the first opening into the space outside of the body; e) coupling the first part of the first device to the second part of the first device in the space outside of the body to make an assembled first device; f) passing the first part of the first device coupled to the second part of the first device back into the body cavity through the first opening; and g) using the first device to perform a procedure within the body cavity. In one embodiment, the method further comprises: a) introducing a second device into the body cavity through the first opening; and b) using the first device and the second device to perform a procedure within the body cavity allowing for triangulation of the first device with respect to the second device. In another embodiment, the method further comprises: a) providing a second device comprising a first part and a second part; b) making a third opening through the body wall and into the body cavity, and where the third opening has a maximum transverse dimension between 0.1 mm and 3 mm and permits introduction of the second part of the second device from the space outside of the body through the third opening and into the body cavity; c) introducing the second part of the second device from the space outside of the body through the third opening into the body cavity; d) passing the second part of the second device from inside of the body cavity through the first opening into the space outside of the body; e) coupling the first part of the second device to the second part of the second device in the space outside of the body to make an assembled second device; f) passing the first part of the second device coupled to the second part of the second device back into the body cavity through the first opening; g) using the second device to perform a procedure within the body cavity. In one embodiment, the method further comprises: a) introducing a third device into the body cavity through the first opening; and b) using the first device, the second device and the third device to perform a procedure within the body cavity allowing for triangulation of the first device with respect to the second device and with respect to the third device. In one embodiment, the method further comprises introducing a first port into the first opening, where the first port extends from the space outside of the body through the body wall and into the body cavity, where the first port has a maximum transverse dimension that permits introduction of the first part of a first device from a space outside of the body through the first port and into the body cavity, and where the first part of the first device has a maximum external transverse dimension greater than 3 mm. In another embodiment, the method further comprises introducing a second port into the second opening, where the second port extends from the space outside of the body through the body wall and into the body cavity, and where the second port has a maximum transverse dimension between 0.1 mm and 3 mm that permits introduction of a second part of the first device from a space outside of the body through the second opening and into the body cavity. In another embodiment, the method further comprises introducing a third port into the third opening, where the third port extends from the space outside of the body through the body wall and into the body cavity, and where the third port has a maximum transverse dimension between 0.1 mm and 3 mm that permits introduction of a second part of the second device from a space outside of the body through the third opening and into the body cavity. In another embodiment, the method further comprises passing the first part of the first device and second part of the first device from the body cavity back through the first opening and into the space outside of the body, uncoupling and removing the first part of the first device from the second part of the first device. In another embodiment, the method further comprises passing the second part of the first device back through the first opening and into the body cavity, and then back through the second opening thereby removing the first part of the first device from the body. In another embodiment, the first part of the first device is a first, first part of the first device, and the method further comprises coupling a second, first part of the first device to the second part of the first device in the space outside of the body to make a second, first device, passing the second, first part of the first device coupled to the second part of the first device back into the body cavity through the first opening and using the second, first device to perform a procedure within the body cavity.

FIGURES

These and other features, aspects and advantages of the present invention will become better understood with regard to the following description, appended claims, and accompanying figures where:

FIG. 4 is a close-up, partial, lateral perspective view of a grasper working end reversibly attached to the distal end of the user interface with the grasper in the open position;

FIG. 7 is a cutaway, close-up, partial, lateral perspective view of a grasper working end reversibly attached to the distal end of the user interface with the grasper in the open position as shown in FIG. 4 taken along the line 7-7;

FIG. 10 is lateral perspective view of the suction device as shown in FIG. 9;

FIG. 11 is a cross-sectional, lateral perspective view of the suction device as shown in FIG. 9 taken along the line 11-11;

DESCRIPTION

According to one embodiment of the present invention, there is provided a device for use in performing minimally invasive surgery. According to another embodiment of the present invention, there is provided a system for performing minimally invasive surgery. The system comprises one or more than one device according to the present invention. According to another embodiment of the present invention, there is provided a method for performing minimally invasive surgery. The method combines the broad usefulness of standard minimally invasive surgery with its multiple incisions that allow triangulation of instrumentation, but with the improved cosmesis of laparoendoscopic single-site surgery, natural orifice transluminal endoscopic surgery and needlescopic surgery. The method is referred to as "scarless microport augmented restoration of triangulation surgery" (SMART surgery). In one embodiment, the method comprises providing a device according to the present invention or providing a system according to the present invention. The device, system and method will now be disclosed in detail.

As used in this disclosure, except where the context requires otherwise, the term "comprise" and variations of the term, such as "comprising," "comprises" and "comprised" are not intended to exclude other additives, components, integers or steps.

As used in this disclosure, the term "minimally invasive surgery" comprises endoscopic surgery (including laparoscopic, retroperitoneoscopic and thoracoscopic surgery, natural orifice surgery, and robotic surgery).

All dimensions specified in this disclosure are by way of example only and are not intended to be limiting. Further, the proportions shown in these Figures are not necessarily to scale. As will be understood by those with skill in the art with reference to this disclosure, the actual dimensions of any device or part of a device disclosed in this disclosure will be determined by the intended use.

As used in this disclosure, except where the context requires otherwise, the method steps disclosed and shown are not intended to be limiting nor are they intended to indicate that each step is essential to the method or that each step must occur in the order disclosed except as specified in this disclosure.

The devices of the present invention and their component parts comprise any suitable material for the intended purpose of the device, as will be understood by those with skill in the art with reference to this disclosure. For example, when the device according to the present invention is used in connection with the method according to the present invention, the device will usually comprise one or more than one biocompatible material capable of being sterilized. Biocompatible refers to a material that can be used with living tissue without toxicity to the living tissue in connection with the use.

Figure 1:
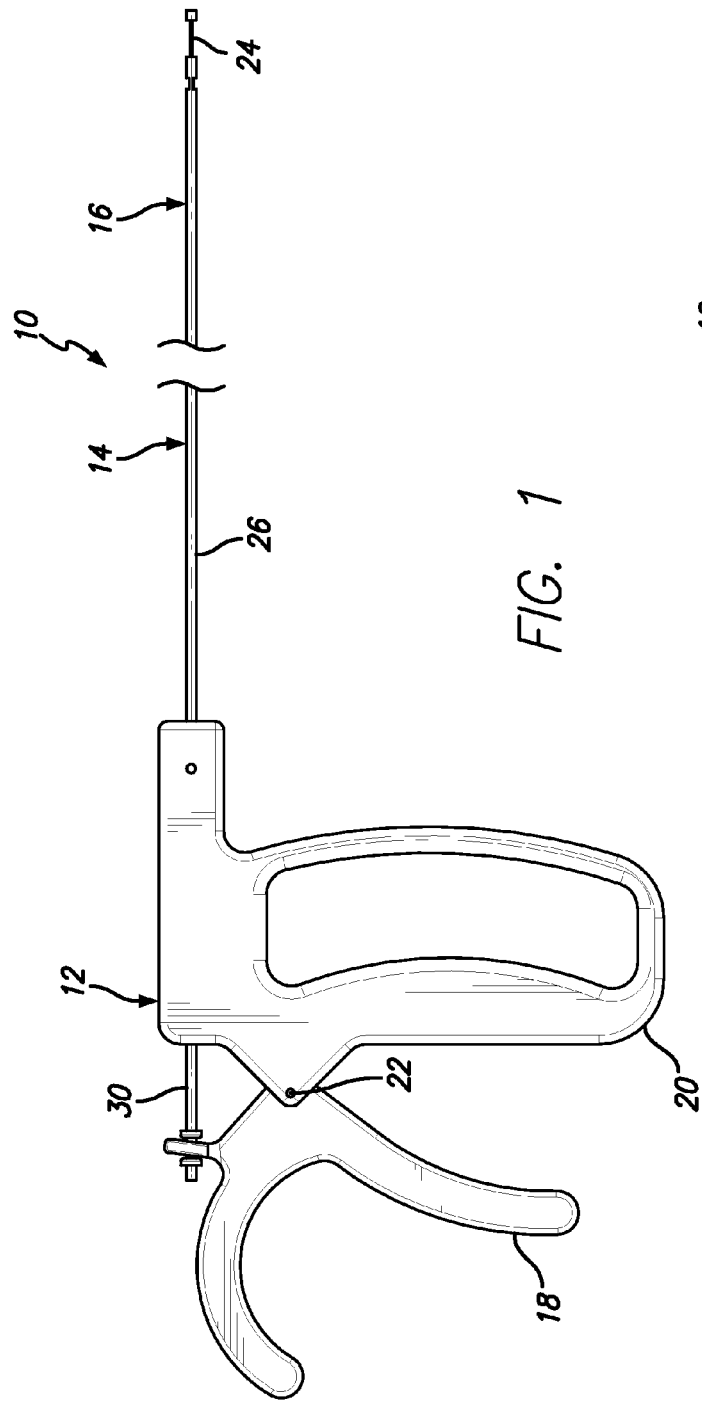
FIG. 1 is a partial, lateral perspective view of a user interface according to the present invention.
Figure 2:
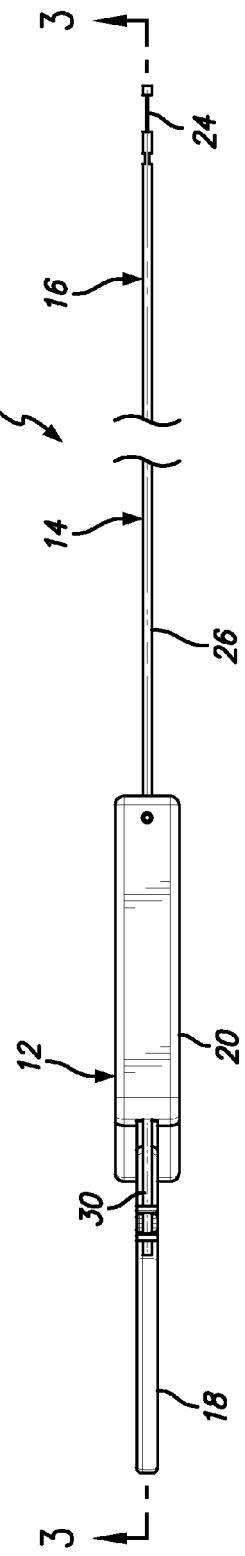
FIG. 2 is a partial, top perspective view of the user interface according to the present invention as shown in FIG. 1.
Figure 3:
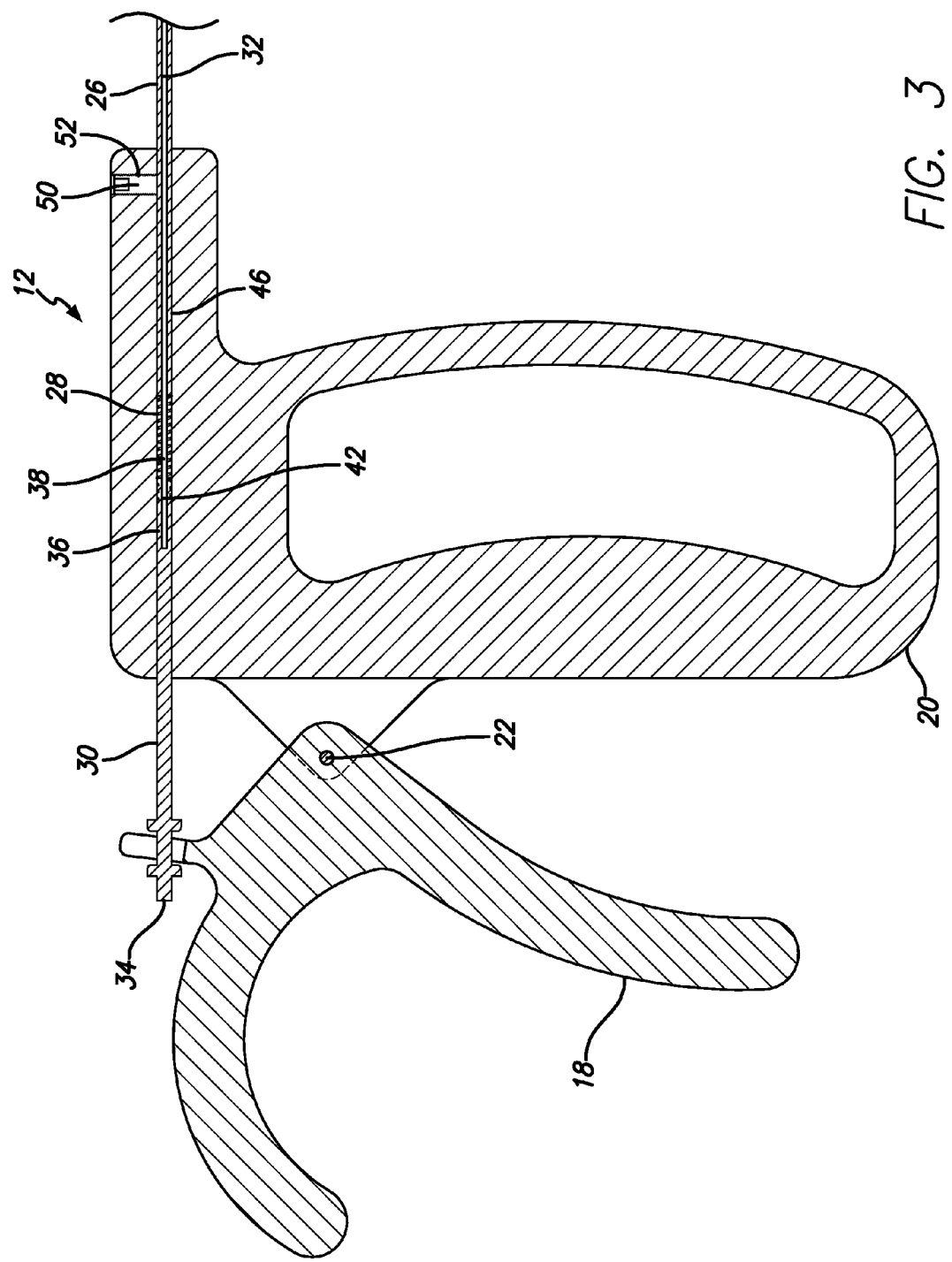
FIG. 3 is a cutaway, partial, lateral perspective view of the proximal end of the user interface according to the present invention as shown in FIG. 1 and FIG. 2 taken along the line 3-3.
Figure 5:
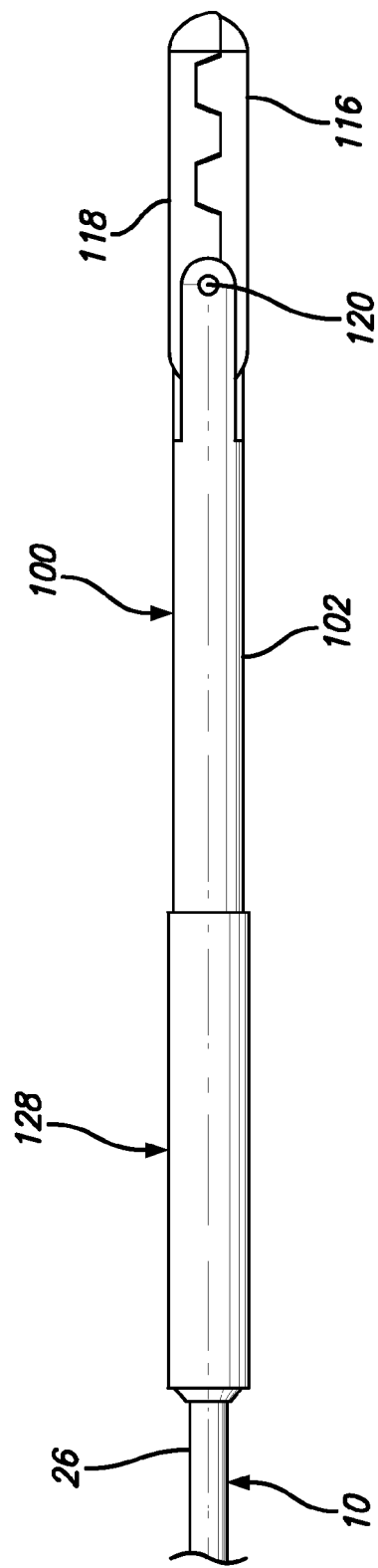
FIG. 5 is a close-up, partial, lateral perspective view of a grasper working end reversibly attached to the distal end of the user interface with the grasper in the closed position.
Figure 6:
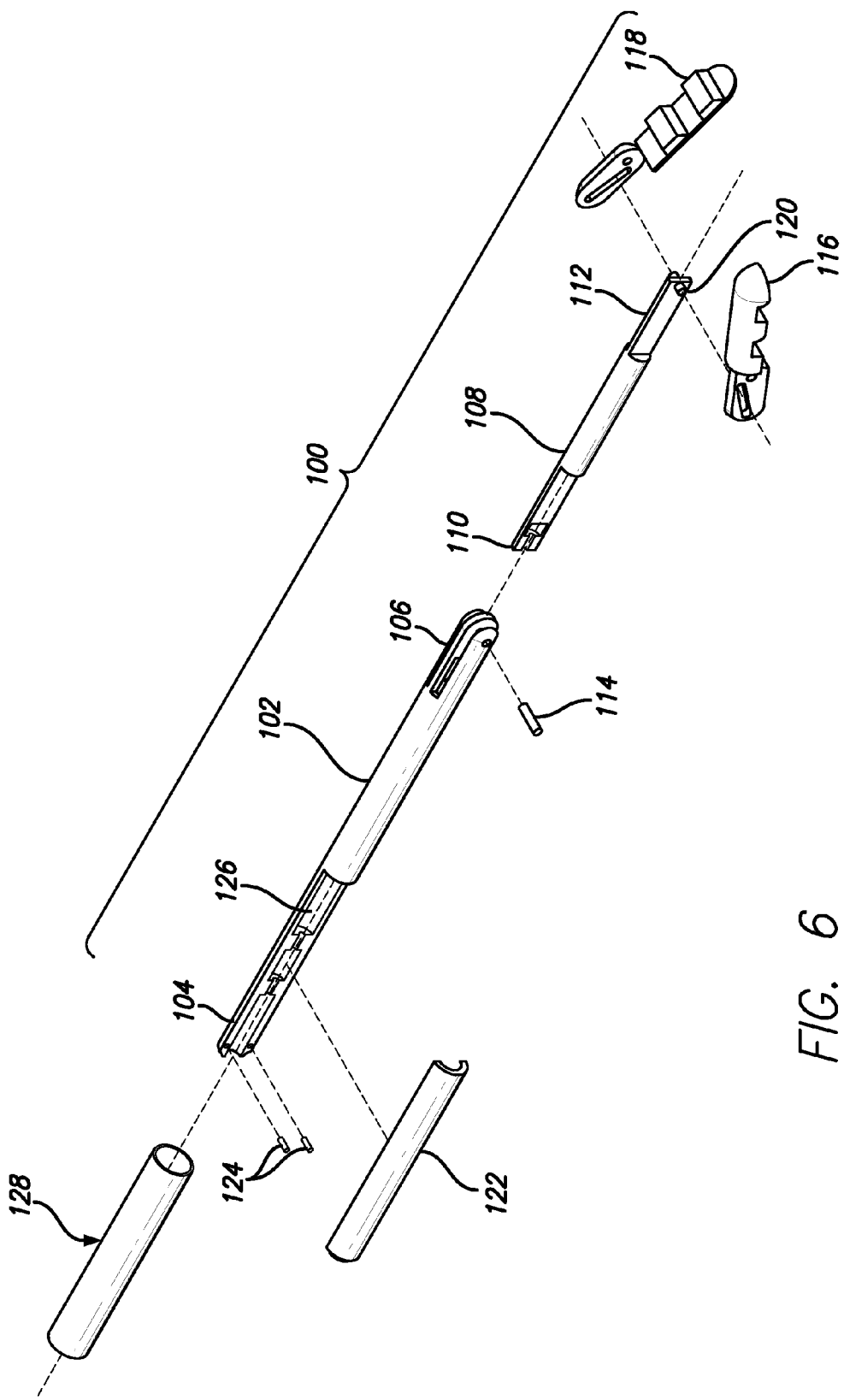
FIG. 6 is an exploded, close-up, partial, lateral perspective view of a grasper working end and the distal end of the user interface as shown in FIG. 4.

According to the present invention, there is provided one or more than one device for use in performing minimally invasive surgery, and in particular for performing a method according to the present invention designated "scarless microport augmented restoration of triangulation surgery" (SMART surgery) in this disclosure. In one embodiment, the one or more than one device is constructed to be sterilizable for reuse on multiple patients. In another embodiment, the one or more than one device is constructed inexpensively and intended to be disposed of after a single use on one patient. Referring now to FIG. 1, FIG. 2 and FIG. 3, there are shown, respectively, a partial, lateral perspective view of a user interface according to the present invention (FIG. 1); a partial, top perspective view of the user interface according to the present invention as shown in FIG. 1 (FIG. 2); and a cutaway, partial, lateral perspective view of the proximal end of the user interface according to the present invention as shown in FIG. 1 and FIG. 2 taken along the line 3-3 (FIG. 3). As can be seen, in one embodiment of the present invention the device is a user interface 10 comprising a proximal portion 12, an intermediate portion 14 and a distal portion 16, where the intermediate portion 14 connects the proximal portion 12 to the distal portion 16. The distal portion 16 is configured to reversibly mate with a working end (such as the grasper working end 100 and the cutting working end 130 disclosed in this disclosure). The proximal portion 12 is configured to allow a user to hold and direct the user interface 10, and to operate the working end attached to the distal portion 16 of the user interface 10 (such as the grasper working end 100 and the cutting working end 130 disclosed in this disclosure).

The proximal portion 12 of the user interface 10 comprises a proximal handle 18 and a distal handle 20 joined together by and rotatable around a pivot 22. As shown, particularly in FIG. 3, the user interface 10 further comprises a pushrod 24, a shaft 26 and a spring 28. The pushrod 24 comprises a proximal portion 30 of the pushrod 24 and a distal portion 32 of the pushrod 24. The proximal portion 30 of the pushrod 24 comprises a proximal end 34 of the proximal portion 30 of the pushrod 24, and comprises a distal end 36 of the proximal portion 30 of the pushrod 24. The proximal end 34 of the proximal portion 30 of the pushrod 24 is linked to the proximal handle 18, such that movement of the proximal handle 18 around the pivot 22 translates into axial movement of the pushrod 24. The distal portion 32 of the pushrod 24 comprises a proximal end 38 of the distal portion 32 of the pushrod 24, and comprises a distal end 40 of the distal portion 32 of the pushrod 24. The distal end 36 of the proximal portion 30 of the pushrod 24 is joined to the proximal end 38 of the distal portion 32 of the pushrod 24 at a junction 42. The distal end 40 of the distal portion 32 of the pushrod 24 comprises an expansion 44 for mating with a working end (such as the grasper working end 100 and the cutting working end 130 disclosed in this disclosure).

The shaft 26 comprises a hollow tubular structure comprising a longitudinal axis and further comprising a proximal portion 46 of the shaft 26 and a distal portion 48 of the shaft 26, where the shaft 26 surrounds at least part of the distal portion 32 of the pushrod 24, where the distal portion 32 of the pushrod 24 is axially slidable within the shaft 26. In one embodiment, the shaft 26 comprises an outer transverse diameter and the outer transverse diameter is between 1 mm and 3 mm. In one embodiment, the shaft 26 comprises an outer transverse diameter and the outer transverse diameter is between 2 mm and 2.2 mm. The spring 28 surrounds the proximal end 38 of the distal portion 32 of the pushrod 24, and the spring 28 is between and abuts the distal end 36 of the proximal portion 30 of the pushrod 24 and the proximal portion 46 of the shaft 26. The user interface 10 further comprises a shaft securing pin 50 configured to insert within a recess 52 in the distal handle 20, thereby securing the shaft 26 from moving relative to the distal handle 20.

According to another embodiment of the present invention, there is provided a working end for performing a function during minimally invasive surgery, where the working end is configured to reversibly mate with the distal end of the distal portion of the user interface. A variety of working ends performing a variety of functions can be provided, as will be understood by those with skill in the art with reference to this disclosure, such as for example a function selected from the group consisting of canulating, clip application, cutting, grasping, lighting, recording images, retracting, sealing, suctioning, and viewing images. In one embodiment, the working end is a grasper working end which performs a grasping and holding function. Referring now to FIG. 4, FIG. 5, FIG. 6 and FIG. 7, there are shown, respectively, a close-up, partial, lateral perspective view of a grasper working end reversibly attached to the distal end of the user interface with the grasper working end in the open position (FIG. 4); a close-up, partial, lateral perspective view of a grasper working end reversibly attached to the distal end of the user interface with the grasper working end in the closed position (FIG. 5); an exploded, close-up, partial, lateral perspective view of a grasper working end and the distal end of the user interface as shown in FIG. 4 (FIG. 6); and a cutaway, close-up, partial, lateral perspective view of a grasper working end reversibly attached to the distal end of the user interface with the grasper working end in the open position as shown in FIG. 4 taken along the line 7-7 (FIG. 7). As can be seen, the grasper working end 100 comprises a head piece 102 comprising a proximal portion 104 of the head piece 102 connected to a distal portion 106 of the head piece 102. The grasper working end 100 further comprises a jaw pushrod 108 comprising a proximal portion 110 of the jaw pushrod 108 and a distal end 112 of the jaw pushrod 108. The distal portion 106 of the head piece 102 is connected to the proximal portion 110 of the jaw pushrod 108 by a jaw pin 114. The grasper working end 100 further comprises a first jaw 116 and a second jaw 118 connected to the distal end 112 of the jaw pushrod 108 by a jaw pivot 120, where the first jaw 116 and the second jaw 118 approximate and separate from each other in response to axial movement of the jaw pushrod 108. The grasper working end 100 further comprises a shaft clamp 122 and one or more than one shaft clamp pins 124 for aligning the shaft clamp 122 with the proximal portion 104 of the head piece 102. The proximal portion 104 of the head piece 102 comprises a recess 126 for mating with the distal portion 48 of the shaft 26 and the distal end 112 of the jaw pushrod 108, where the distal portion 48 of the shaft 26 and the distal end 112 of the jaw pushrod 108 are secured to the head piece 102 by placing the shaft clamp 122 onto the proximal portion 104 of the head piece 102 and securing the shaft clamp 122 onto the proximal portion 104 of the head piece 102 by threading a threaded fastener 128 over both the shaft clamp 122 and the proximal portion 104 of the head piece 102.

Figure 8:
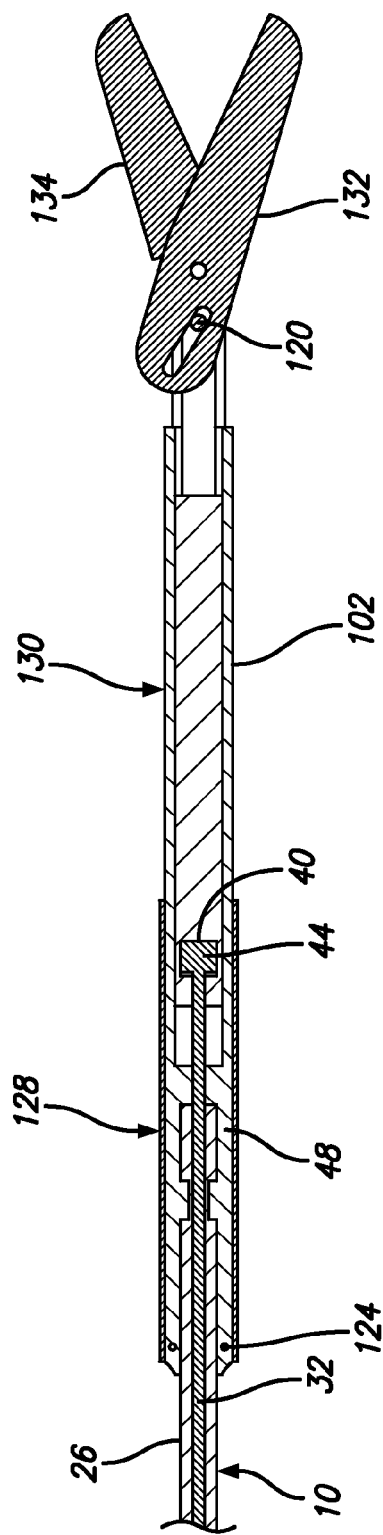
FIG. 8 is a cutaway, close-up, partial, lateral perspective view of a cutting working end according to the present invention reversibly attached to the distal end of the user interface with the cutting working end in the open position.

In another embodiment of the present invention, there is provided another working end for performing a function during minimally invasive surgery, where the working end is configured to reversibly mate with the distal portion 16 of the user interface 10. In this embodiment, the working end is a cutting working end which performs a cutting function. Referring now to FIG. 8, there is shown a cutaway, close-up, partial, lateral perspective view of a cutting working end according to the present invention reversibly attached to the distal end of the user interface with the cutting working end in the open position. As can be seen, the cutting working end 130 comprises the same elements as the grasper working end 100, except that the cutting working end 130 comprises a first blade 132 and a second blade 134, instead of a first jaw 116 and the second jaw 118. Like the first jaw 116 and the second jaw 118, the first blade 132 and the second blade 134 approximate and separate from each other in response to axial movement of the jaw pushrod 108.

Figure 9:
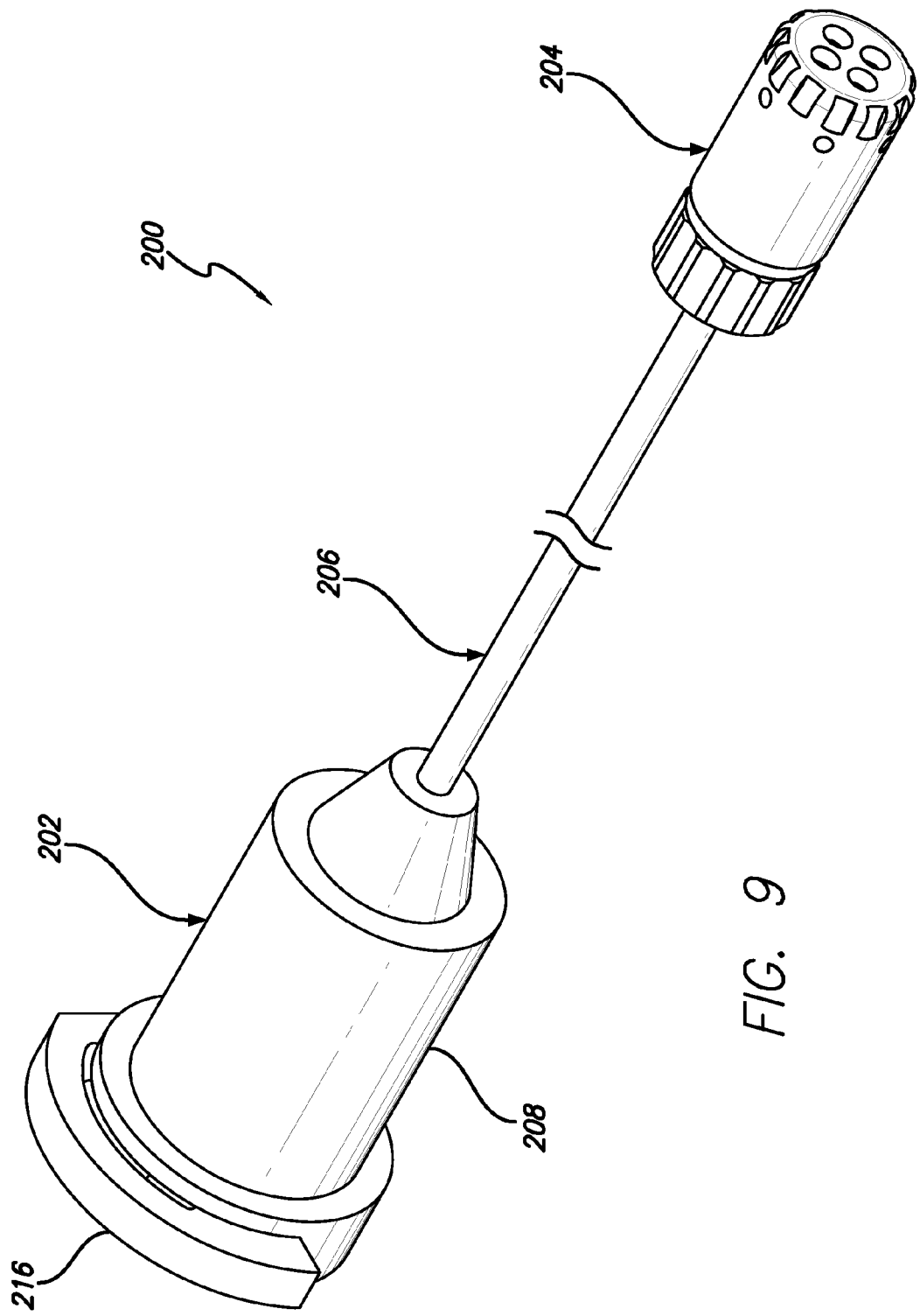
FIG. 9 is a partial, frontal-lateral perspective view of a suction device according to the present invention.
Figure 12:
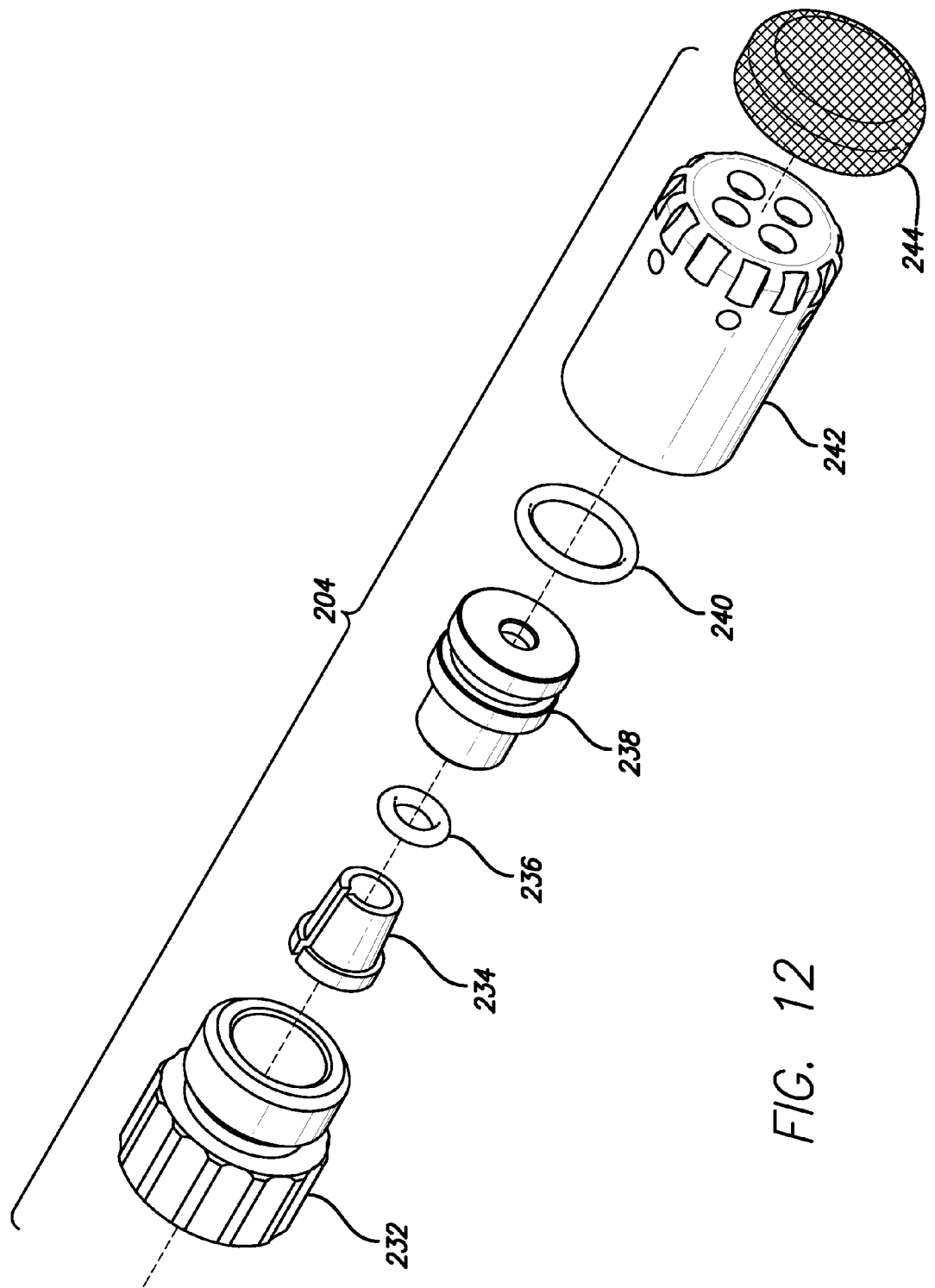
FIG. 12 is an exploded, frontal-lateral perspective view of the distal end of the suction device shown in FIG. 9.

According to another embodiment of the present invention, the device according to the present invention is a suction device for performing a suction function during minimally invasive surgery. Referring now to FIG. 9, FIG. 10, FIG. 11 and FIG. 12, there are shown, respectively, a partial, frontal-lateral perspective view of a suction device according to the present invention (FIG. 9); a lateral perspective view of the suction device as shown in FIG. 9 (FIG. 10); a cross-sectional, lateral perspective view of the suction device as shown in FIG. 9 taken along the line 11-11 (FIG. 11); and an exploded, frontal-lateral perspective view of the distal end of the suction device shown in FIG. 9 (FIG. 12). As can be seen, the suction device 200 comprises a suction connector 202 proximally, a distal suction head 204 distally and a suction shaft 206 connecting the suction connector 202 to the suction head 204. The suction connector 202 comprises a joining piece 208 comprising a proximal end 210 of the joining piece 208 and a distal end 212 of the joining piece 208, and further comprises a central cavity 214 within the joining piece 208 between the proximal end 210 of the joining piece 208 and the distal end 212 of the joining piece 208. The suction connector 202 further comprises a circlip 216. During use, a source of suction (not shown) such as a suction hose is inserted through the proximal end 210 of the joining piece 208 and into central cavity 214. The circlip 216 is then clamped onto the joining piece 208 and grips the source of suction thereby holding the source of suction in place in the joining piece 208 creating continuity between the source of suction and the suction shaft 206.

The suction shaft 206 comprises a hollow tubular structure comprising a proximal end 218 of the suction shaft 206, a distal end 220 of the suction shaft 206, an intermediate section 222 of the suction shaft 206 connecting the proximal end 218 of the suction shaft 206 to the distal end 220 of the suction shaft 206, an inner surface 224 of the suction shaft 206, an outer surface 226 of the suction shaft 206, a wall 228 of the suction shaft 206 defined between the inner surface 224 of the suction shaft 206 and the outer surface 226 of the suction shaft 206, a central lumen 230 of the suction shaft 206 defined by the inner surface 224 of the suction shaft 206, an outer transverse diameter defined by the outer surface 226 of the suction shaft 206 and an inner transverse diameter defined by the inner surface 224 of the suction shaft 206. In one embodiment, the outer transverse diameter of the suction shaft 206 is between 1 mm and 3 mm. In another embodiment, the outer transverse diameter of the suction shaft 206 is between 2 mm and 2.5 mm. In another embodiment, the outer transverse diameter of the suction shaft 206 is 2.25 mm. In one embodiment, the inner transverse diameter of the suction shaft 206 is between 1 mm and 3 mm. In another embodiment, the inner transverse diameter of the suction shaft 206 is between 1.5 mm and 2 mm. In another embodiment, the inner transverse diameter of the suction shaft 206 is 1.95 mm.

The suction head 204 comprises, from proximal to distal as shown particularly in FIG. 11 and FIG. 12, a fastener 232, a shaft clamp 234, a shaft clamp o-ring 236, a clamp funnel 238, a clamp funnel o-ring 240 and a suction tip 242. When assembled, as shown, the distal end 220 of the suction shaft 206 passes within the fastener 232, the shaft clamp 234, the shaft clamp o-ring 236, the clamp funnel 238, and the clamp funnel o-ring 240 and is fixed in position, allowing suction from the source of suction to be delivered to the suction tip 242, and externally therethrough.

In one embodiment, the suction device 200 further comprises a fine mesh 244 covering the suction tip 242 which assists in preventing occlusion of the suction tip by body tissues such as fat and momentum and by blood clots during use.

Figure 13:
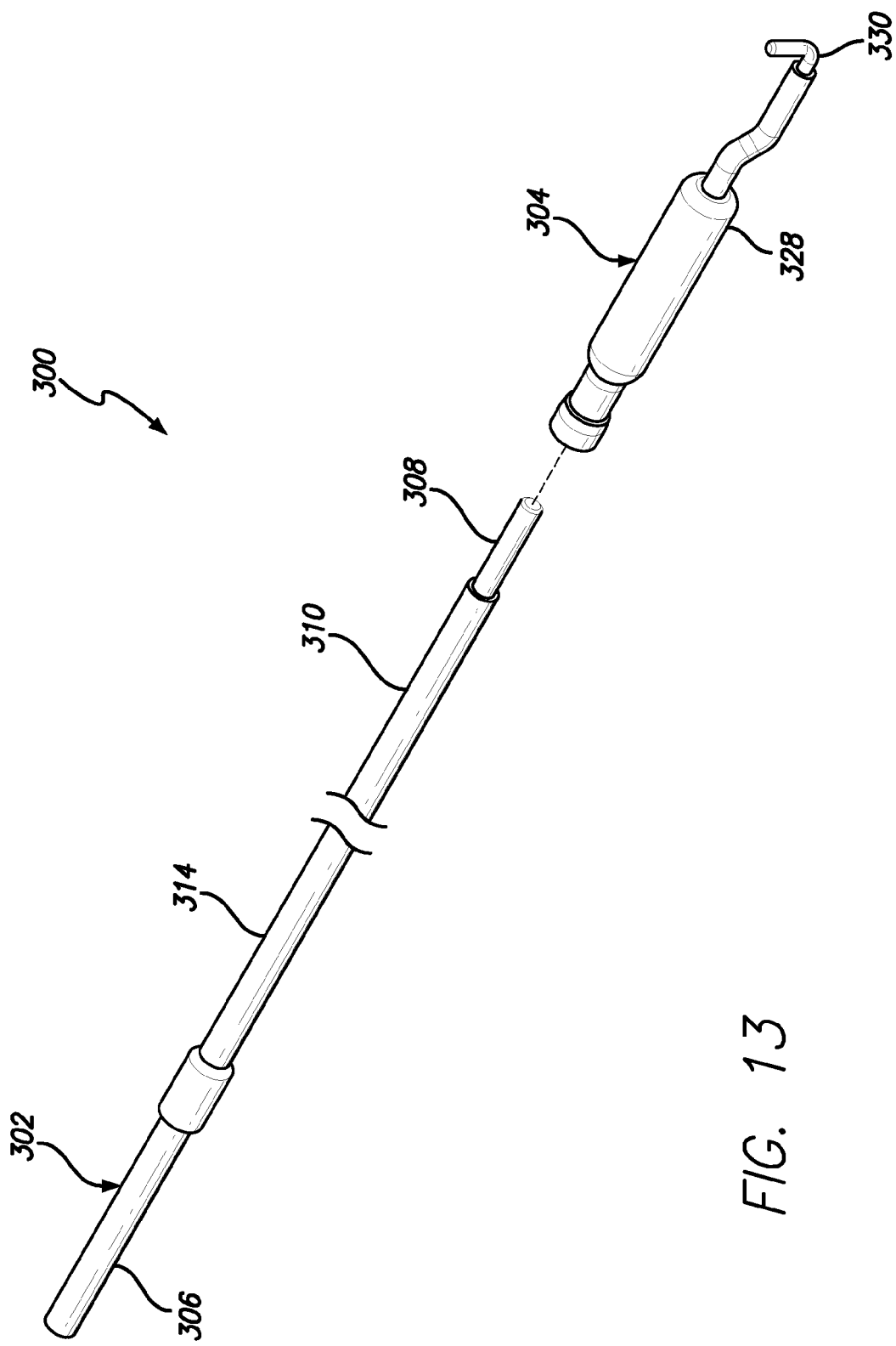
FIG. 13 is a partial, frontal-lateral perspective view of an electrocautery assembly according to the present invention.
Figure 14:
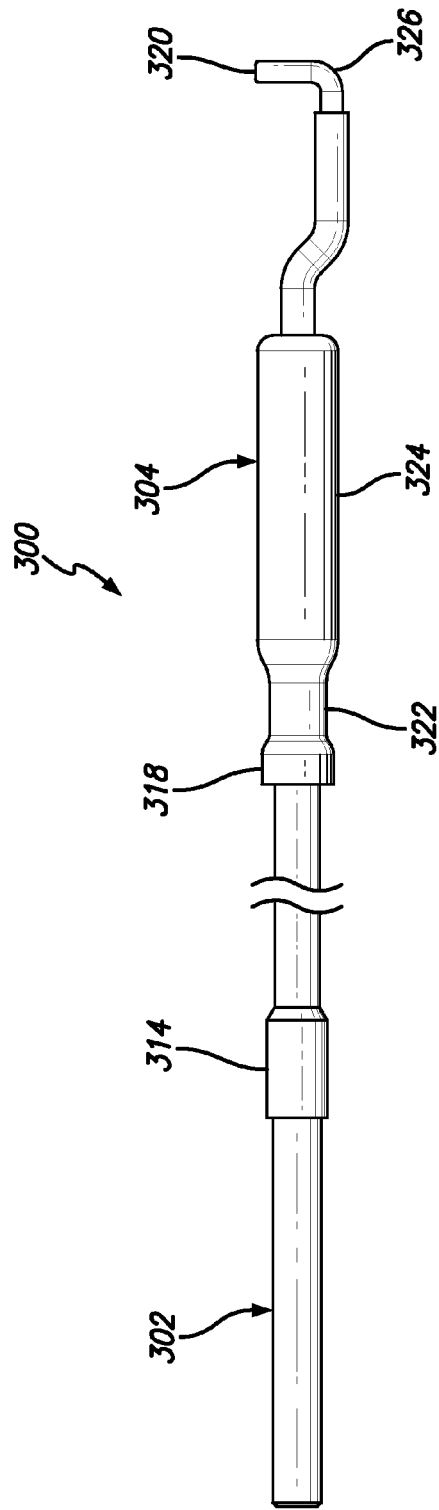
FIG. 14 is a partial, lateral perspective view of the distal end of the electrocautery assembly according to the present invention as shown in FIG. 13.
Figure 15:
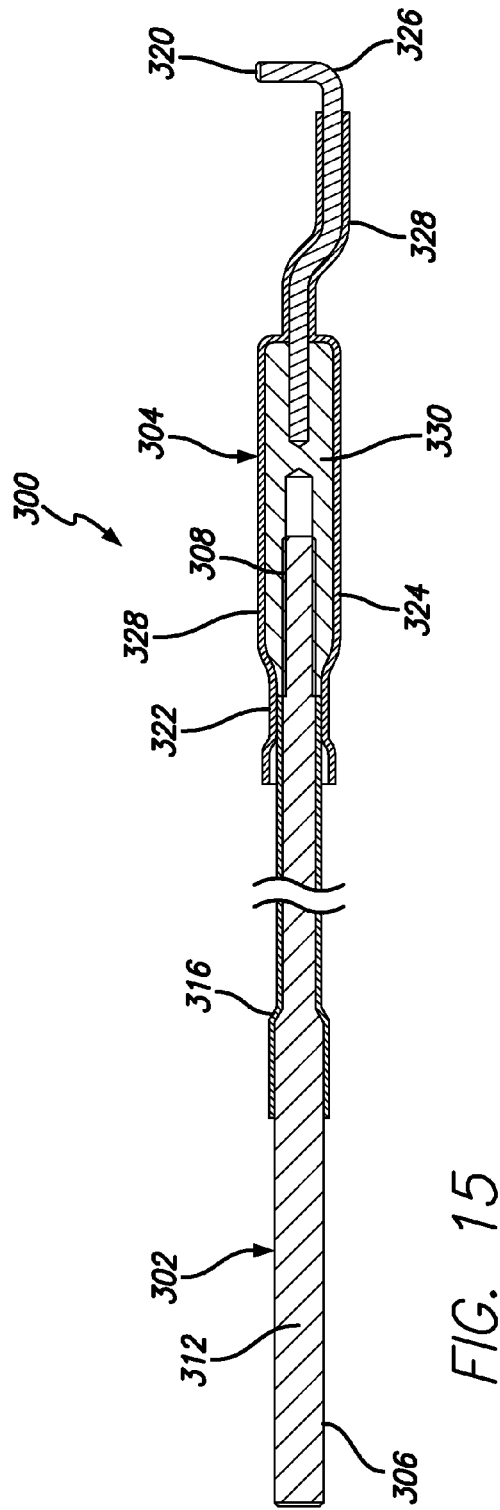
FIG. 15 is a cutaway, partial, lateral perspective view of the distal end of the electrocautery assembly according to the present invention as shown in FIG. 13 and FIG. 14 taken along the line 15-15.

In another embodiment of the present invention, there is provided an electrocautery assembly for performing electrocautery during minimally invasive surgery. Referring now to FIG. 13, FIG. 14 and FIG. 15, there are shown, respectively, a partial, frontal-lateral perspective view of an electrocautery assembly according to the present invention (FIG. 13); a partial, lateral perspective view of the distal end of the electrocautery assembly according to the present invention as shown in FIG. 13 (FIG. 14); and a cutaway, partial, lateral perspective view of the distal end of the electrocautery assembly according to the present invention as shown in FIG. 13 and FIG. 14 taken along the line 15-15 (FIG. 15). As can be seen, in one embodiment the electrocautery assembly 300 device is an electrocautery device for sealing blood vessels, dissecting tissue, cutting and cauterization. The electrocautery assembly 300 comprises an electrocautery assembly shaft 302 proximally configured to reversibly mate with an electrocautery assembly head 304 distally. The electrocautery assembly shaft 302 comprises a cylindrical structure comprising a proximal end 306 of the electrocautery assembly shaft 302, a distal end 308 of the electrocautery assembly shaft 302, an intermediate section 310 of the electrocautery assembly shaft 302 connecting the proximal end 306 of the electrocautery assembly shaft 302 to the distal end 308 of the electrocautery assembly shaft 302. The electrocautery assembly shaft 302 further comprises a central core 312 extending from the proximal end 306 of the electrocautery assembly shaft 302 to the distal end 308 of the electrocautery assembly shaft 302, and an insulation casing 314 surrounding the central core 312 in the intermediate section 310, where the insulation casing 314 comprises an outer surface 316 of the insulation casing 314. The electrocautery assembly shaft 302 further comprises an outer transverse diameter defined by the outer surface 316 of the electrocautery assembly shaft 302. The central core 312 comprises material suitable for transmitting an electric charge from the proximal end 306 of the electrocautery assembly shaft 302 to the distal end 308 of the electrocautery assembly shaft 302, as will be understood by those with skill in the art with reference to this disclosure. The insulation casing 314 of the electrocautery assembly shaft 302 comprises material suitable to insulate any electric charge in the central core 312 from the external environment, as will be understood by those with skill in the art with reference to this disclosure. In one embodiment, the outer transverse diameter of the electrocautery assembly shaft 302 is between 1 mm and 3 mm. In another embodiment, the outer transverse diameter of the electrocautery assembly shaft 302 is between 2 mm and 2.5 mm. In another embodiment, the outer transverse diameter of the electrocautery assembly shaft 302 is 2.3 mm.

The electrocautery assembly head 304 comprises a proximal end 318 of the electrocautery assembly head 304, and a distal end 320 of the electrocautery assembly head 304, and comprises from the proximal end 318 of the electrocautery assembly head 304 to the distal end 320 of the electrocautery assembly head 304, a proximal section 322 of the electrocautery assembly head 304 connected to an intermediate section 324 of the electrocautery assembly head 304 connected to a distal section 326 of the electrocautery assembly head 304. The electrocautery assembly head 304 further comprises an insulation casing 328 of the electrocautery assembly head 304 and a central core 330 of the electrocautery assembly head 304, where the insulation casing 328 of the electrocautery assembly head 304 surrounds the core 330 in the proximal section 322 of the electrocautery assembly head 304 and the intermediate section 324 of the electrocautery assembly head 304, and where the distal section 326 of the electrocautery assembly head 304 comprises the core 330 of the electrocautery assembly head 304. The proximal section 322 of the electrocautery assembly head 304 is a hollow tubular structure defined by the insulation casing 328 and is configured to mate with the distal end 308 of the electrocautery assembly shaft 302, such as for example by being threaded onto the distal end 308 of the electrocautery assembly shaft 302. The distal end 308 of the electrocautery assembly shaft 302 fits into a matching recess in the intermediate section 324 of the electrocautery assembly head 304 as shown particularly in FIG. 15 thereby making electrical contact with the core 330 of the electrocautery assembly head 304. The core 330 comprises material suitable for transmitting an electric charge from the distal end 308 of the electrocautery assembly shaft 302 to the distal end 320 of the electrocautery assembly head 304 and therethrough to living tissue, as will be understood by those with skill in the art with reference to this disclosure. The insulation casing 328 of the electrocautery assembly head 304 comprises material suitable to insulate any electric charge in the core 330 from the external environment, as will be understood by those with skill in the art with reference to this disclosure.

The proximal end 306 of the electrocautery assembly shaft 302 is configured to mate with the distal end of a standard electrocautery unit as used in open minimally invasive surgery often referred to as a "Bovie." The distal end 308 of the electrocautery assembly shaft 302 is configured to mate with the proximal section 322 of the electrocautery assembly head 304 such as for example by being threaded onto the proximal section 322 of the electrocautery assembly head 304. Electric current from the distal end of a standard electrocautery unit passes through the core 312 of the electrocautery assembly shaft 302 and into the core 330 of the electrocautery assembly head 304 thereby transmitting an electric current from the distal end of an electrocautery unit to the distal end 308 of the electrocautery assembly shaft 302 to the distal section 326 of the electrocautery assembly 300 and therethrough to living tissue.

According to another embodiment of the present invention, there is provided a system for performing minimally invasive surgery. The system comprises one or more than one device according to the present invention. In one embodiment, the system comprises written or recorded directions for using the one or more than one device. In one embodiment, the system comprises two devices according to the present invention. In one embodiment, the system comprises a user interface according to the present invention and further comprises a working end that mates with the user interface according to the present invention. In a preferred embodiment, the system is used to perform a method according to the present invention which minimizes scarring on the abdominal wall while providing for adequate triangulation of the devices from different angles during the method.

According to another embodiment of the present invention, there is provided a method for performing a form of minimally invasive surgery referred to as "scarless microport augmented restoration of triangulation surgery" (SMART surgery). In summary, scarless microport augmented restoration of triangulation surgery comprises making two or more than two openings, such as a first opening and a second opening into a body wall, where the body wall separates a body cavity within the body from a space outside of the body. The first opening has a maximum size that permits the introduction of a first part of a first device having a maximum external transverse dimension greater than 3 mm into the body cavity. The second opening has a maximum size that permits the introduction of a second part of the first device having a maximum external transverse dimension between 0.1 mm and 3 mm but no greater than 3 mm into the body cavity. The method comprises introducing the second part of the first device having a maximum external transverse dimension between 0.1 mm and 3 mm through the second opening and into the body cavity, passing the second part of the first device through the first opening into the space outside of the body, coupling the first part of the first device to the second part of the first device in the space outside of the body to make an assembled first device, and passing the first part of the first device coupled to the second part of the first device back into the body cavity through the first opening thereby making a functional first device within the body cavity. In one embodiment, a second device is introduced into the body cavity through the first opening, and the first device and the second device are then used to perform a procedure within the body cavity allowing for triangulation of the first device with respect to the second device. In a preferred embodiment, the method further comprises making a third opening. The third opening has a maximum size that permits the introduction of a second part of a second device having a maximum external transverse dimension between 0.1 mm and 3 mm but no greater than 3 mm into the body cavity, and the method further comprises introducing the second part of the second device having a maximum external transverse dimension between 0.1 mm and 3 mm through the third opening and into the body cavity, passing the second part of the second device through the first opening into the space outside of the body, coupling the first part of the second device to the second part of the second device in the space outside of the body to make an assembled second device, and passing the first part of the second device coupled to the second part of the second device back into the body cavity through the first opening thereby making a functional second device within the body cavity. The first device and the second device are then used to perform a procedure within the body cavity allowing for triangulation of the first device with respect to the second device. In a preferred embodiment, the method further comprises introducing a third device through the first opening and into the body cavity, and the first device, second device and third device are then used to perform a procedure within the body cavity allowing for triangulation of the first device with respect to the second device and with respect to the third device. The method will now be disclosed in additional detail.

According to another embodiment of the present invention, there is provided a method for performing a form of minimally invasive surgery, referred to as "scarless microport augmented restoration of triangulation surgery" (SMART surgery), in a body cavity within a living body, where the body cavity is separated from a space outside of the body by a body wall. Referring now to FIG. 16 through FIG. 32 there are shown some steps in a method for performing minimally invasive surgery according to the present invention, where 400 is a body wall (in this case an abdominal wall) separating a body cavity 402 from the space outside of the body 404, 406 is a first opening, 408 is a second opening, 410 is a first port in the first opening, 412 is a second port in the second opening, 414 is the first part of a first device, 416 is the second part of the first device, 418 is a standard surgical suction apparatus, 420 is a third opening, 422 is a third port in the third opening, 424 is the first part of a second device, 426 is the second part of the second device and 428 is the second, first part of the first device to the second part of the first device.

In one embodiment, the body cavity is selected from the group consisting of an abdominal cavity, a pelvic cavity and a thoracic cavity. In one embodiment, the body wall is selected from the group consisting of an abdominal wall, a colonic wall, an esophageal wall, a thoracic wall, a tracheal wall, an oral wall and a vaginal wall. In one embodiment, the living body is a living human body.

The method comprises providing a first device comprising a first part and a second part, where the first part of the first device has a maximum external transverse dimension greater than 3 mm, and where the second part of the first device has a maximum external transverse dimension of between 0.1 mm and 3 mm. In one embodiment, the first device is a device according to the present invention. In one embodiment, the first part of the first device is a working end according to the present invention, and the second part of the first device is an intermediate portion of a user interface according to the present invention. In one embodiment, the first device is a suction device according to the present invention, and the first part of the first device is a suction head, and the second part of the first device is a suction shaft. In one embodiment, the first device is an electrocautery assembly according to the present invention, and the first part of the first device is the electrocautery assembly head, and the second part of the first device is the electrocautery assembly shaft. In a preferred embodiment, the method further comprises providing a second device. In one embodiment, the second device comprises a first part and a second part, where the first part of the second device has a maximum external transverse dimension greater than 3 mm, and where the second part of the second device has a maximum external transverse dimension of between 0.1 mm and 3 mm. In one embodiment, the second device is a device according to the present invention. In one embodiment, the first part of the second device is a working end according to the present invention, and the second part of the second device is an intermediate portion of a user interface according to the present invention. In one embodiment, the second device is a suction device according to the present invention, and the first part of the second device is a suction head, and the second part of the second device is a suction shaft. In one embodiment, the second device is an electrocautery assembly according to the present invention, and the first part of the second device is the electrocautery assembly head, and the second part of the second device is the electrocautery assembly shaft. In another embodiment, the first device or the second device is selected from the group consisting of a canulator, a clip applied, a cutter, a grasper, an image recorder, an image viewer, a retractor, a sealer and a suction.

Figure 16:
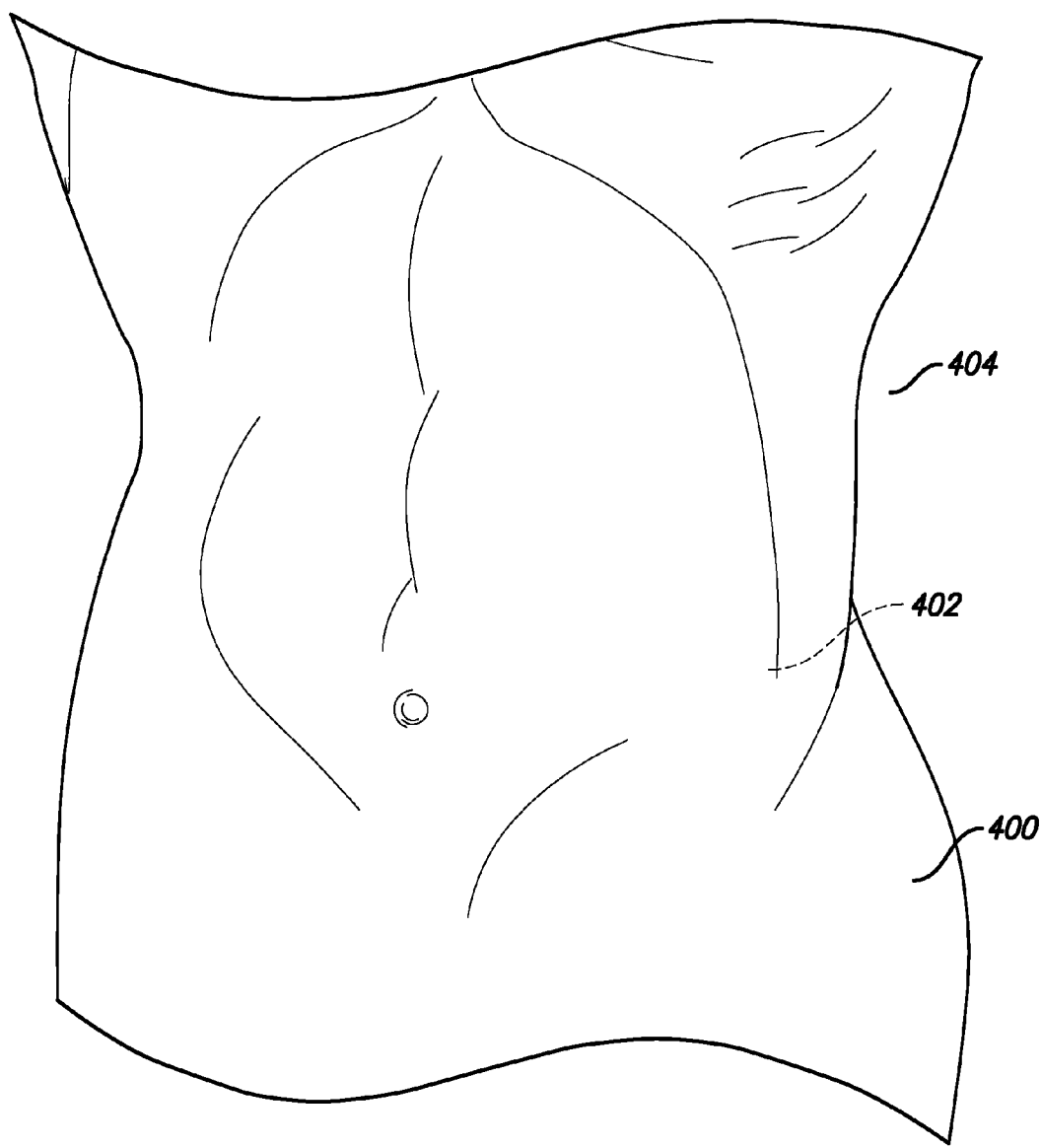
FIG. 16 through FIG. 32 show some steps in a method for performing minimally invasive surgery according to the present invention.
Figure 17:
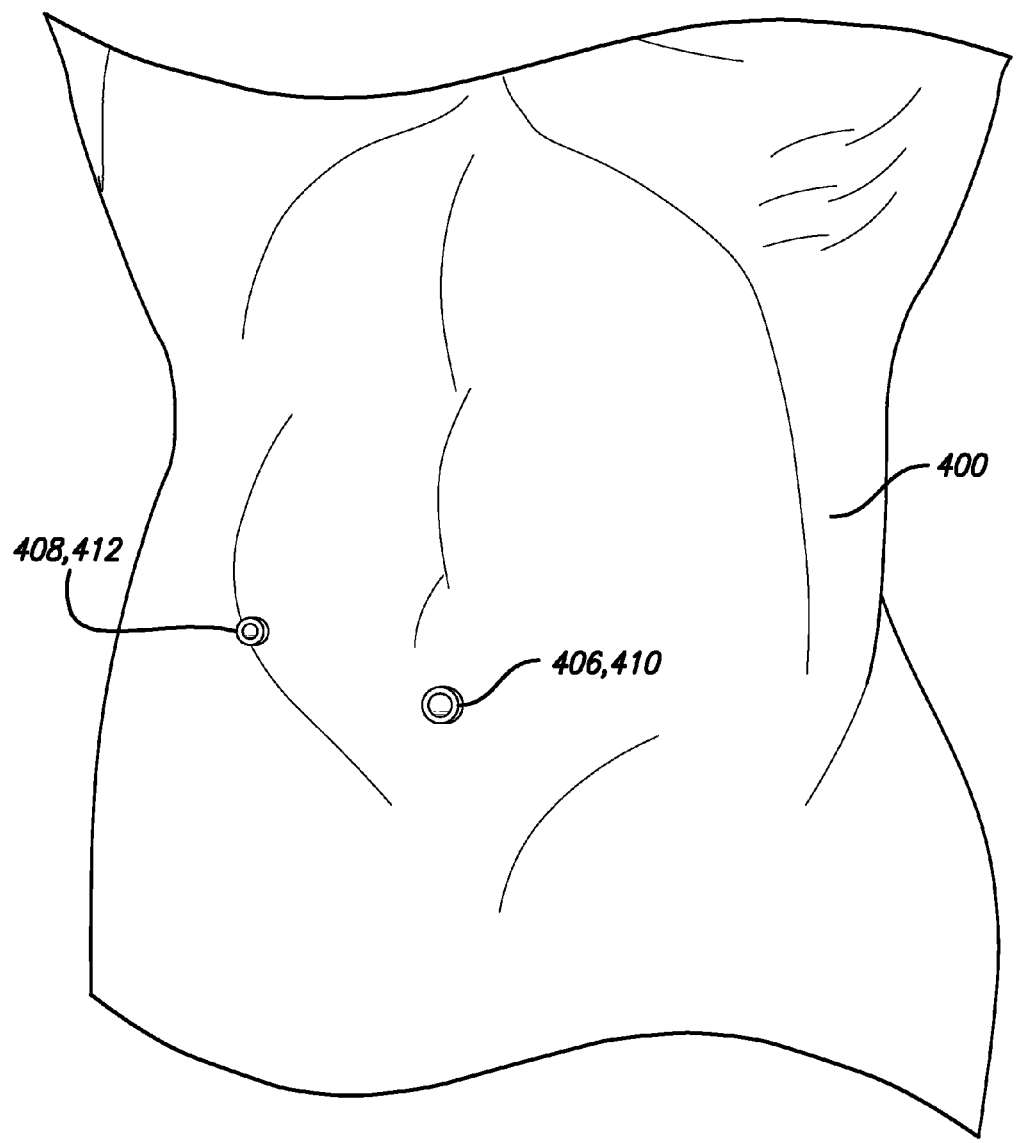
Figure 18:
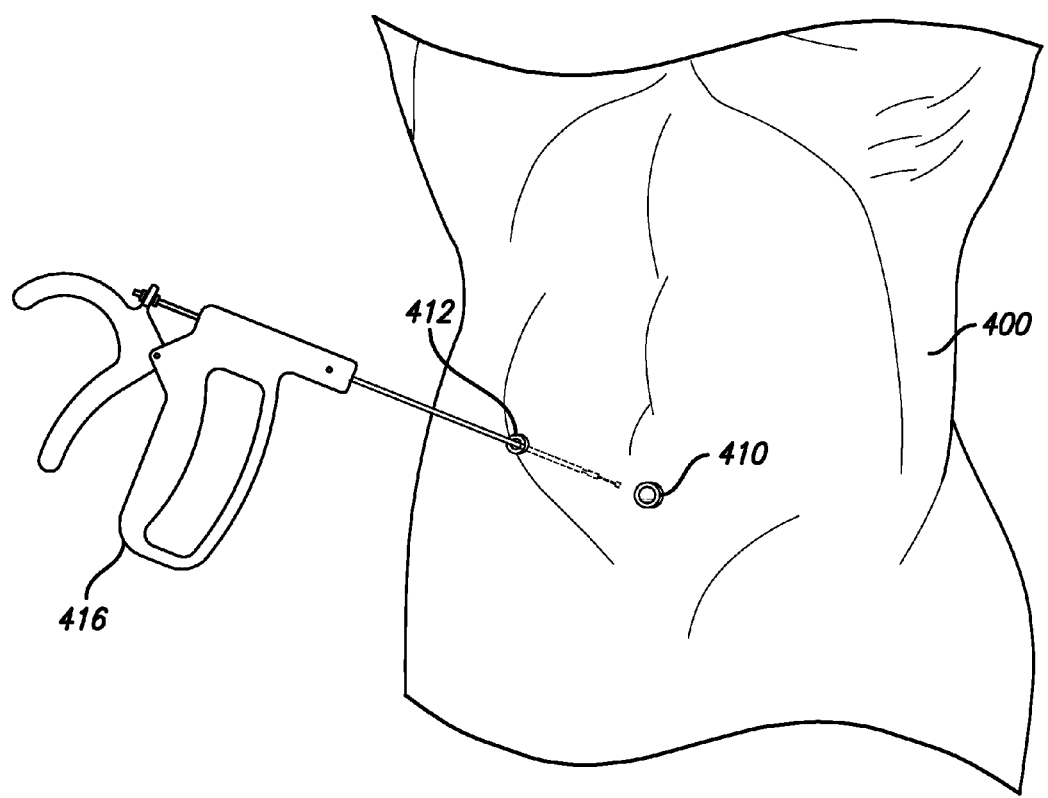
Figure 19:
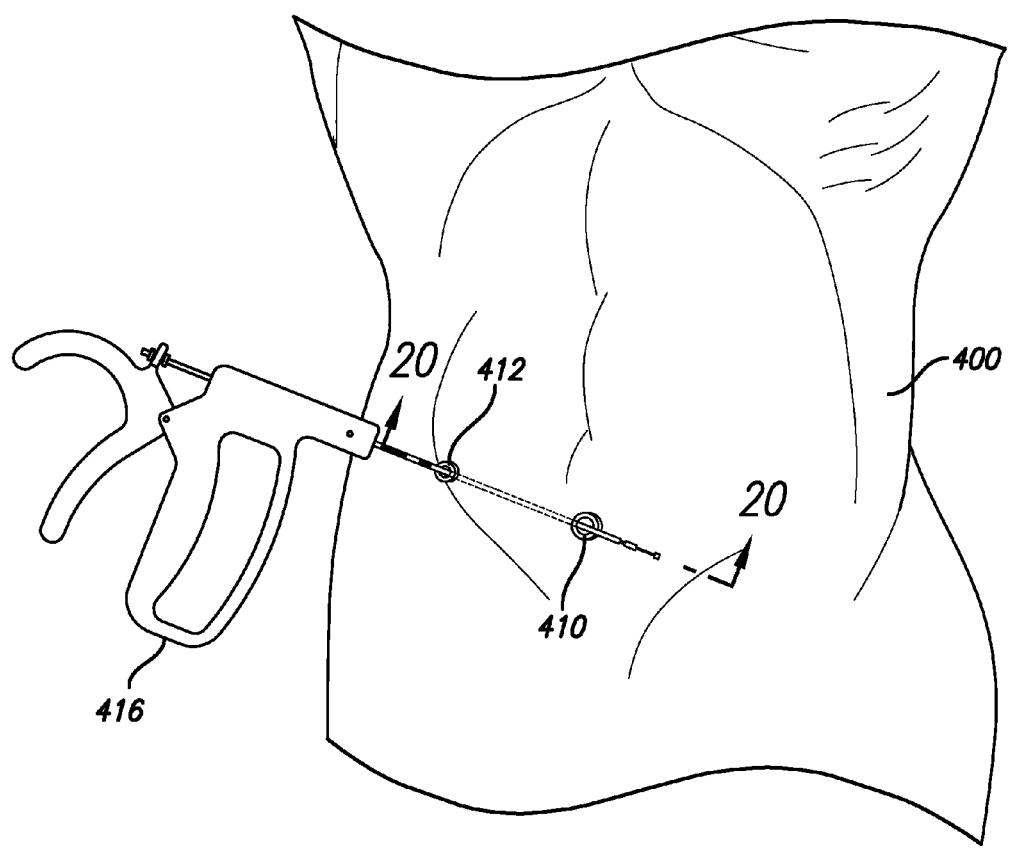
Figure 20:
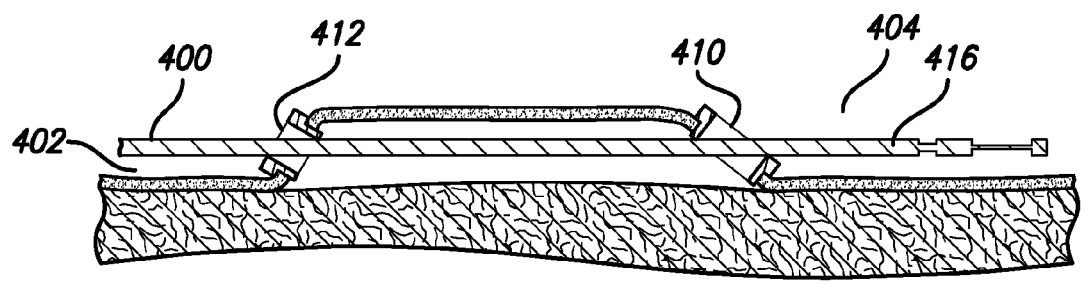
Figure 21:
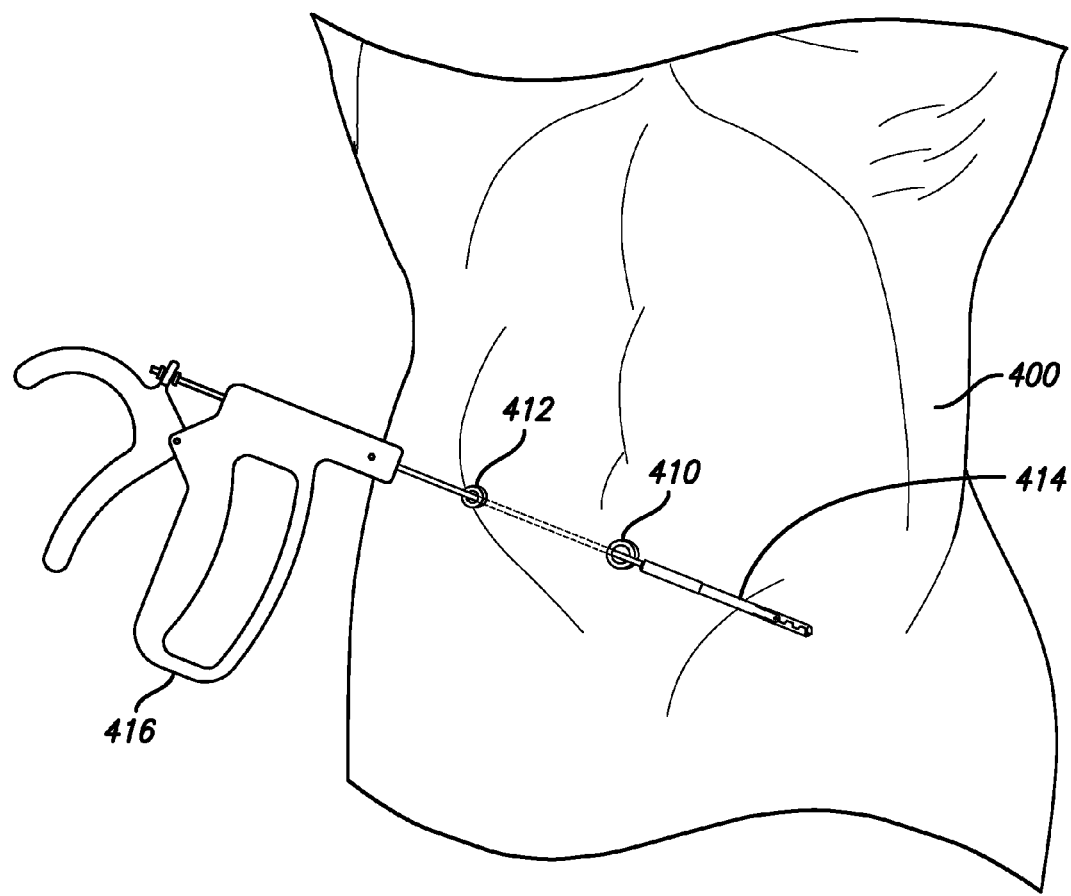
Figure 22:
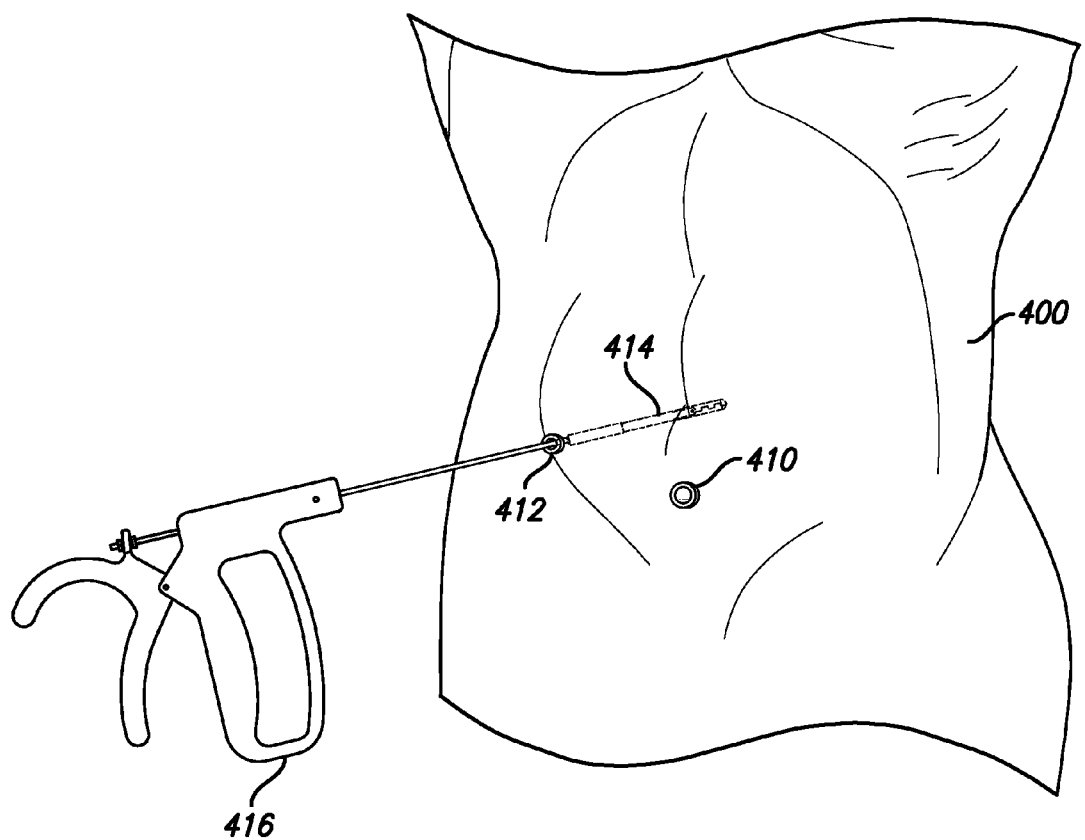

Referring now to the Figures, and in particular FIG. 16 and FIG. 17, the method comprises making two or more than two openings, such as a first opening and a second opening into a body wall (in this case an abdominal wall), where the body wall separates a body cavity within the body from a space outside of the body. In one embodiment, the two or more than two openings consist of between two openings and fifty openings into the body wall. In another embodiment, the two or more than two openings consist of between two openings and twenty openings into the body wall. In another embodiment, the two or more than two openings consist of between two openings and ten openings into the body wall. In another embodiment, the two or more than two openings consist of between two openings and five openings into the body wall. In another embodiment, the two or more than two openings consist of four openings into the body wall. In another embodiment, the two or more than two openings consist of three openings into the body wall. In another embodiment, the two or more than two openings consist of two openings into the body wall.

The method comprises making a first opening through the body wall and into the body cavity. In one embodiment, the first opening is made using a surgical scalpel. In another embodiment, the first opening is made using a no-scalpel technique. In another embodiment, the first opening is made using a trocar. In one embodiment, the body wall is an abdominal wall and the first opening is made in an abdominal wall through an umbilicus or through an umbilical crease. The first opening has a maximum transverse dimension that permits introduction of the first part of the first device from the space outside of the body through the first opening and into the body cavity, where the first part of the first device has a maximum external transverse dimension greater than 3 mm, such as for example where the first part of the first device has a maximum external transverse dimension of between 3 mm and 50 mm. As will be understood by those with skill in the art with reference to this disclosure, the maximum transverse dimension of an opening in the body wall is measured with respect to the surface of the body wall, not with respect to the thickness of the body wall. In one embodiment, the method further comprises introducing a first port into the first opening, where the first port extends from the space outside of the body through the body wall and into the body cavity. The first port has a maximum transverse dimension that permits introduction of the first part of a first device from a space outside of the body through the first port and into the body cavity, where the first part of the first device has a maximum external transverse dimension greater than 3 mm, such as for example where the first part of the first device has a maximum external transverse dimension of between 3 mm and 50 mm. As will be understood by those with skill in the art with reference to this disclosure, the maximum transverse dimension of a port is measured with respect to surface of the body wall once the port is placed, not with respect to the thickness of the body wall. In one embodiment, the first part of the first device has a maximum external transverse dimension between 3 mm and 50 mm. In another embodiment, the first part of the first device has a maximum external transverse dimension between 5 mm and 50 mm. In another embodiment, the first part of the first device has a maximum external transverse dimension between 3 mm and 20 mm. In another embodiment, the first part of the first device has a maximum external transverse dimension between 3 mm and 12 mm. In another embodiment, the first part of the first device has a maximum external transverse dimension between 5 mm and 10 mm. In another embodiment, the first part of the first device has a maximum external transverse dimension between 20 mm and 30 mm. In one embodiment, the first opening has a maximum transverse dimension of between 3 mm and 80 mm. In another embodiment, the first opening has a maximum transverse dimension of between 3 mm and 50 mm. In another embodiment, the first opening has a maximum transverse dimension of between 5 mm and 50 mm. In another embodiment, the first opening has a maximum transverse dimension of between 3 mm and 20 mm. In another embodiment, the first opening has a maximum transverse dimension of between 3 mm and 12 mm. In another embodiment, the first opening has a maximum transverse dimension of between 5 mm and 10 mm. In another embodiment, the first opening has a maximum transverse dimension of between 20 mm and 30 mm. In one embodiment, the first port has a maximum transverse dimension of between 3 mm and 80 mm. In another embodiment, the first port has a maximum transverse dimension of between 3 mm and 50 mm. In another embodiment, the first port has a maximum transverse dimension of between 5 mm and 50 mm. In another embodiment, the first port has a maximum transverse dimension of between 3 mm and 20 mm. In another embodiment, the first port has a maximum transverse dimension of between 3 mm and 12 mm. In another embodiment, the first port has a maximum transverse dimension of between 5 mm and 10 mm. In another embodiment, the first port has a maximum transverse dimension of between 20 mm and 30 mm. The larger maximum transverse dimensions of the first opening and first port are used when a large tissue such as an intact kidney is removed through the first opening using the present method, or when multiple devices are introduced into the first opening or first port simultaneously, as will be understood by those with skill in the art with reference to this disclosure.

Then, the method comprises making a second opening through the body wall and into the body cavity. In one embodiment, the second opening is made using a surgical scalpel. In another embodiment, the first opening is made using a no-scalpel technique. In another embodiment, the second opening is made using a trocar. The second opening has a maximum transverse dimension between 0.1 mm and 3 mm and permits introduction of a second part of the first device from the space outside of the body through the second opening and into the body cavity. In one embodiment, the method further comprises introducing a second port into the second opening, where the second port extends from the space outside of the body through the body wall and into the body cavity, and where the second port has a maximum transverse dimension between 0.1 mm and 3 mm that permits introduction of a second part of the first device from a space outside of the body through the second opening and into the body cavity. In one embodiment, the second part of the first device has a maximum external transverse dimension between 0.1 mm and 3 mm. In another embodiment, the second part of the first device has a maximum external transverse dimension between 1 mm and 3 mm. In another embodiment, the second part of the first device has a maximum external transverse dimension between 2 mm and 3 mm. In another embodiment, the second part of the first device has a maximum external transverse dimension of 2.5 mm. In one embodiment, the second opening has a maximum transverse dimension of between 1 mm and 3 mm. In another embodiment, the second opening has a maximum transverse dimension of between 2 mm and 3 mm. In another embodiment, the second opening has a maximum transverse dimension of 2.5 mm. In one embodiment, the second port has a maximum transverse dimension of between 1 mm and 3 mm. In another embodiment, the second port has a maximum transverse dimension of between 2 mm and 3 mm. In another embodiment, the second port has a maximum transverse dimension of 2.5 mm.

Figure 24:
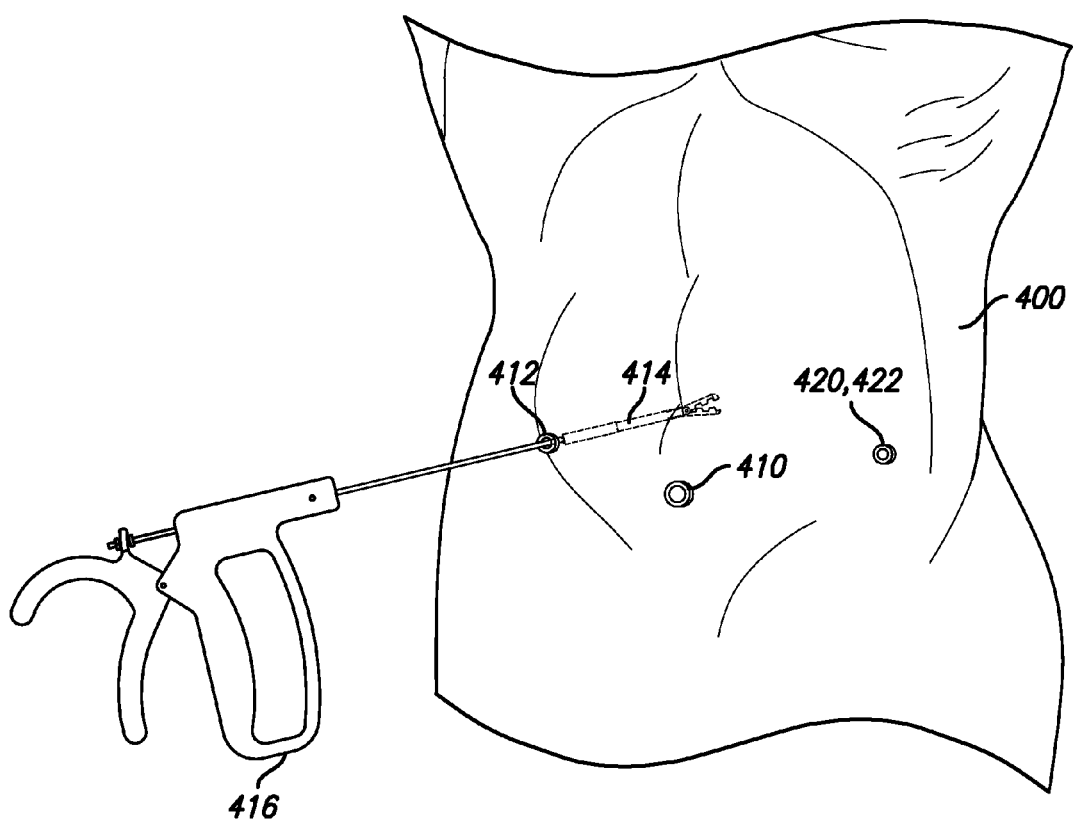
Figure 25:
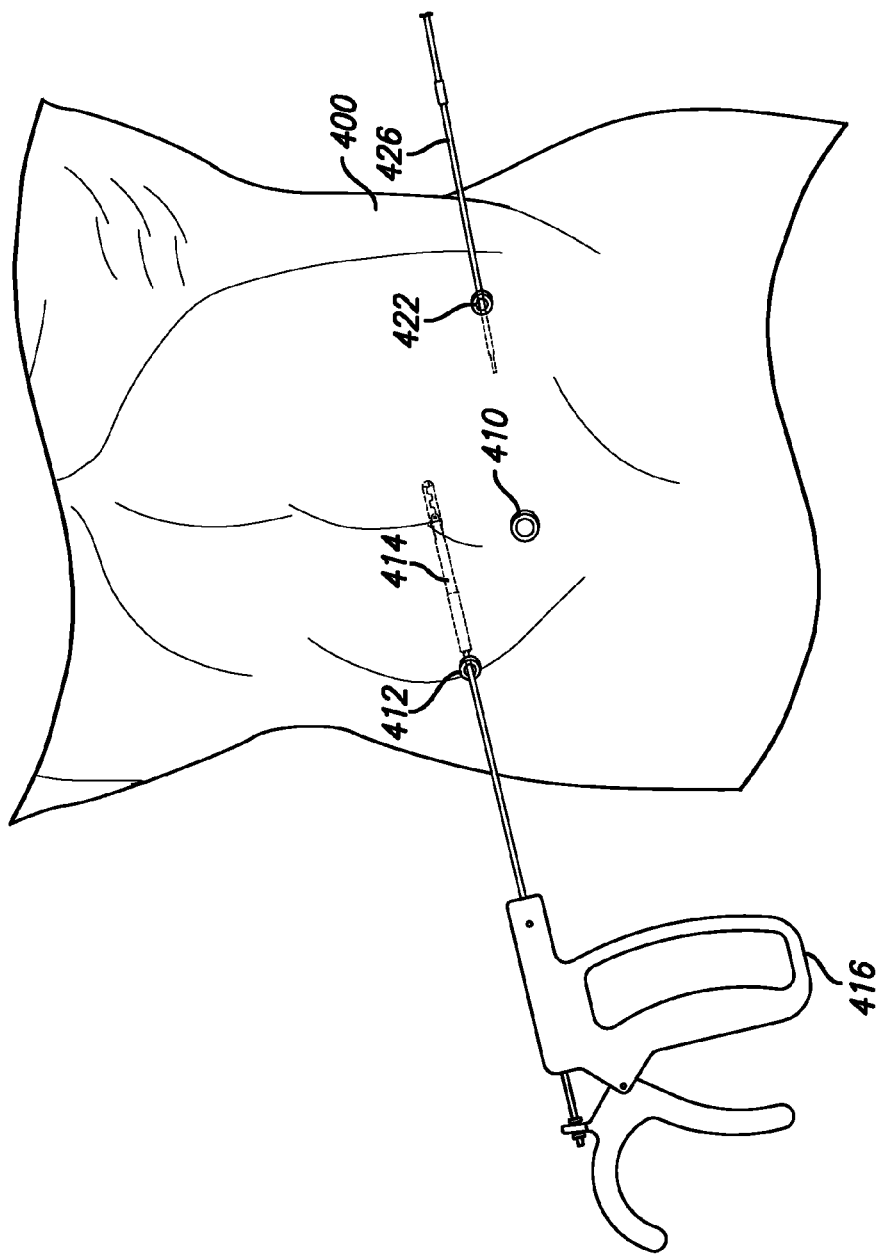
Figure 26:
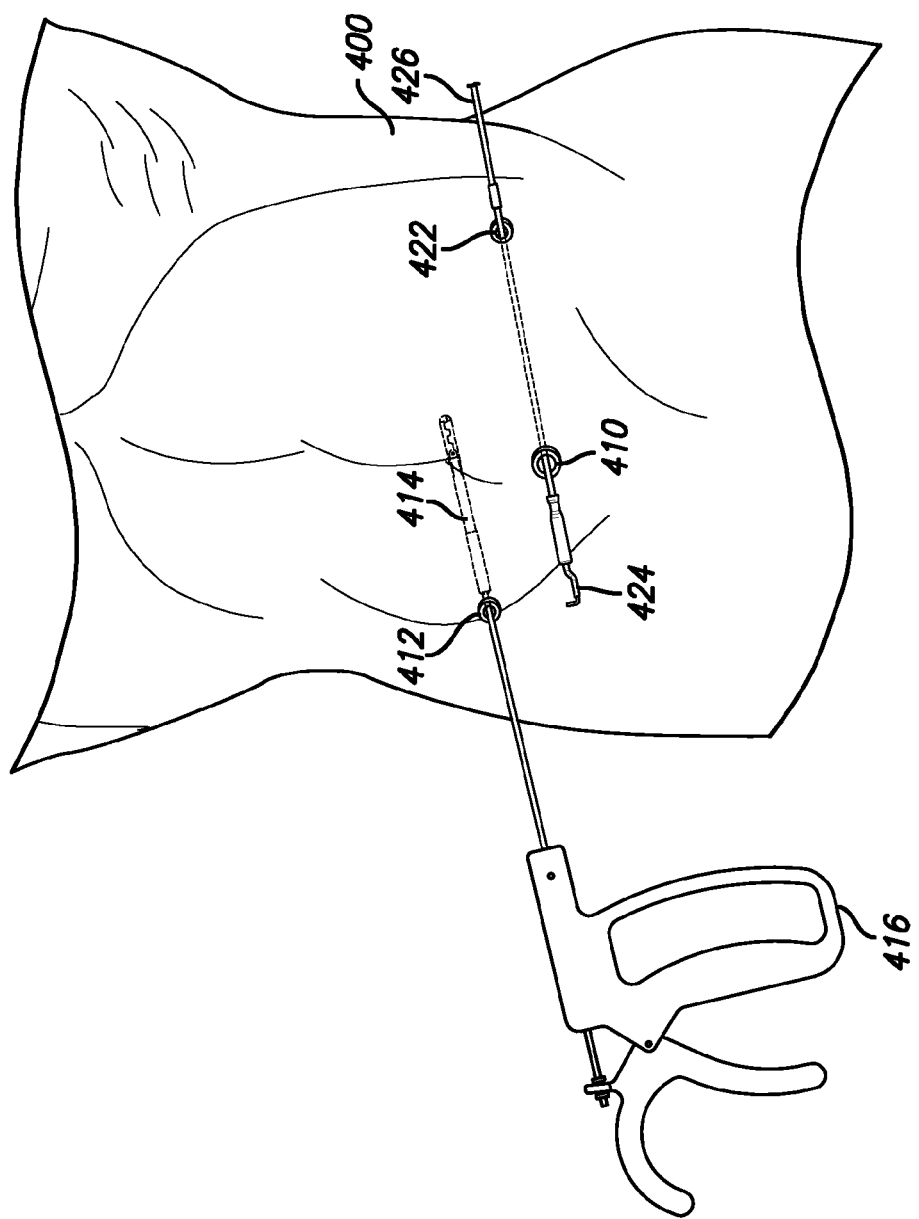
Figure 27:
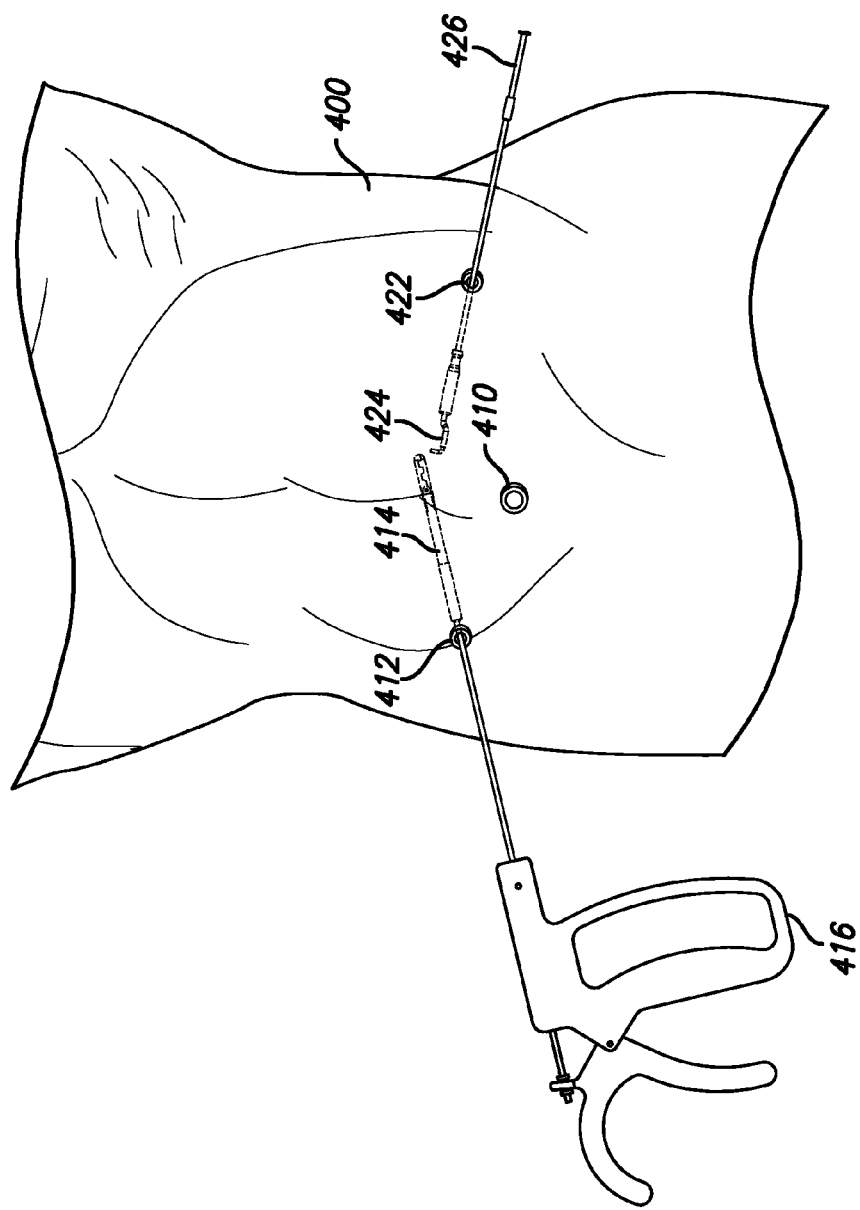
Figure 28:
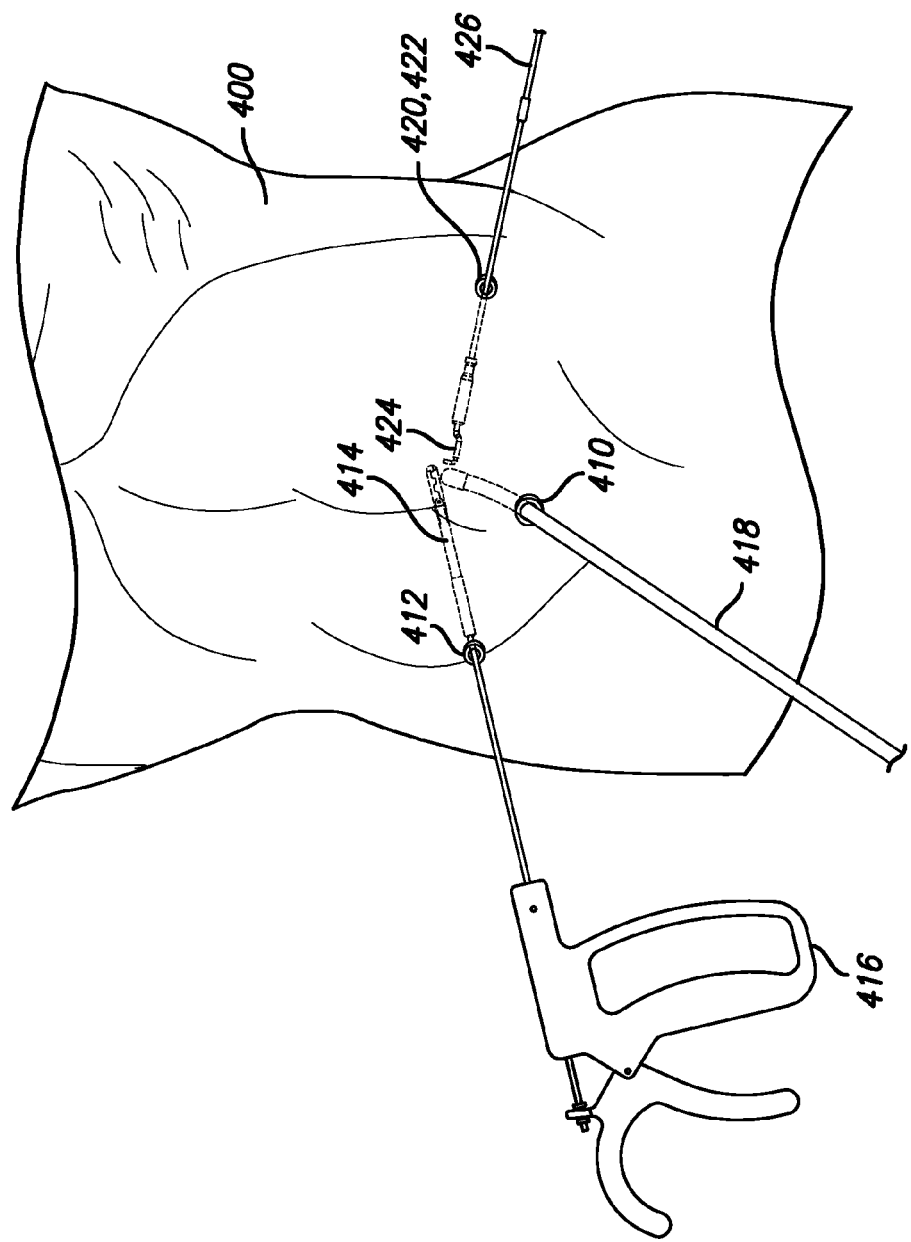

In a preferred embodiment, the method further comprises making a third opening through the body wall and into the body cavity, as shown particularly in FIG. 24. In one embodiment, the third opening is made using a surgical scalpel. In another embodiment, the first opening is made using a no-scalpel technique. In another embodiment, the third opening is made using a trocar. The third opening has a maximum transverse dimension between 0.1 mm and 3 mm and permits introduction of a second part of the second device from the space outside of the body through the third opening and into the body cavity. In one embodiment, the method further comprises introducing a third port into the third opening, where the third port extends from the space outside of the body through the body wall and into the body cavity, and where the third port has a maximum transverse dimension between 0.1 mm and 3 mm that permits introduction of a second part of the second device from a space outside of the body through the third opening and into the body cavity. In one embodiment, the second part of the second device has a maximum external transverse dimension between 0.1 mm and 3 mm. In another embodiment, the second part of the second device has a maximum external transverse dimension between 1 mm and 3 mm. In another embodiment, the second part of the second device has a maximum external transverse dimension between 2 mm and 3 mm. In another embodiment, the second part of the second device has a maximum external transverse dimension of 2.5 mm. In one embodiment, the third opening has a maximum transverse dimension of between 1 mm and 3 mm. In another embodiment, the third opening has a maximum transverse dimension of between 2 mm and 3 mm. In another embodiment, the third opening has a maximum transverse dimension of 2.5 mm. In one embodiment, the third port has a maximum transverse dimension of between 1 mm and 3 mm. In another embodiment, the third port has a maximum transverse dimension of between 2 mm and 3 mm. In another embodiment, the third port has a maximum transverse dimension of 2.5 mm.

Figure 23:
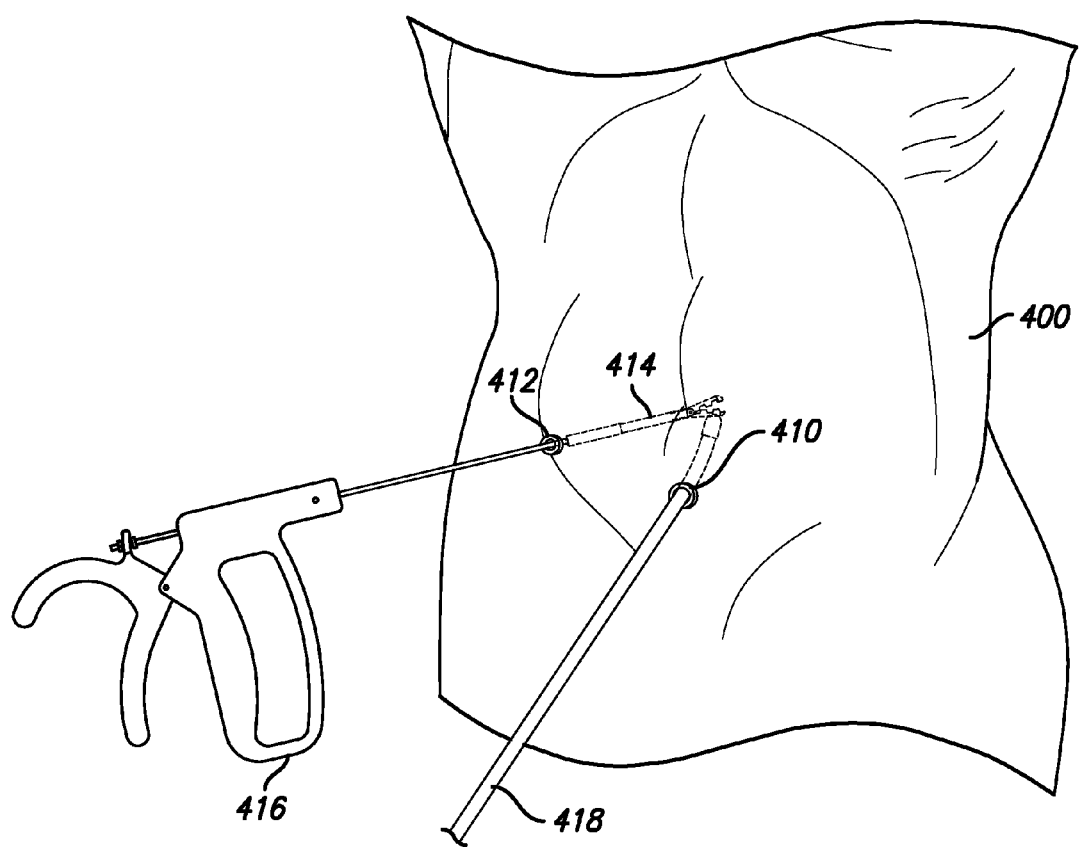

Next, as can be seen particularly in FIG. 18 through FIG. 22, the method further comprises introducing the second part of the first device from the space outside of the body through the second opening (and through the second port when present) into the body cavity, passing the second part of the first device from inside of the body cavity through the first opening (and through the first port when present) into the space outside of the body, coupling the first part of the first device to the second part of the first device in the space outside of the body to make an assembled first device, and passing the first part of the first device coupled to the second part of the first device back into the body cavity through the first opening (and through the first port when present). In one embodiment, as can be seen in FIG. 23, the method further comprises introducing a second device (such as a standard surgical suction apparatus shown in FIG. 23) into the body cavity through the first opening (and through the first port when present), and the first device and the second device are then used to perform a procedure within the body cavity allowing for triangulation of the first device with respect to the second device.

In a preferred embodiment, as can be seen particularly in FIG. 14 through FIG. 27, the method further comprises providing a second device comprising a first part and a second part; making the third opening through the body wall and into the body cavity, introducing the second part of the second device from the space outside of the body through the third opening (and through the third port when present) into the body cavity, passing the second part of the second device from inside of the body cavity through the first opening (and through the first port when present) into the space outside of the body, coupling the first part of the second device to the second part of the second device in the space outside of the body to make an assembled second device, and passing the first part of the second device coupled to the second part of the second device back into the body cavity through the first opening (and through the first port when present). The first device and the second device are then used to perform a procedure within the body cavity allowing for triangulation of the first device with respect to the second device. In a preferred embodiment, as can be seen particularly in FIG. 28, the method further comprises introducing a third device (such as a standard surgical suction apparatus shown in FIG. 28) into the body cavity through the first opening (and through the first port when present), and the first device, the second device and the third device are then used to perform a procedure within the body cavity allowing for triangulation of the first device with respect to the second device and with respect to the third device.

Figure 29:
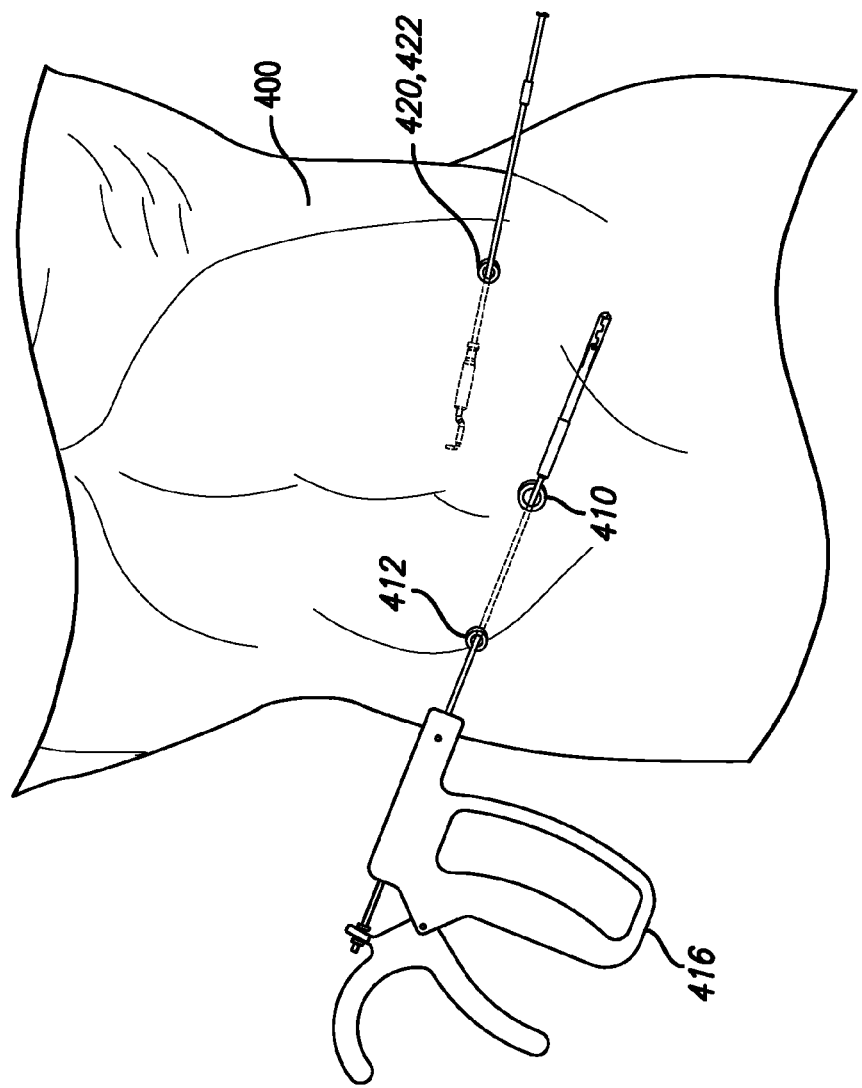
Figure 30:
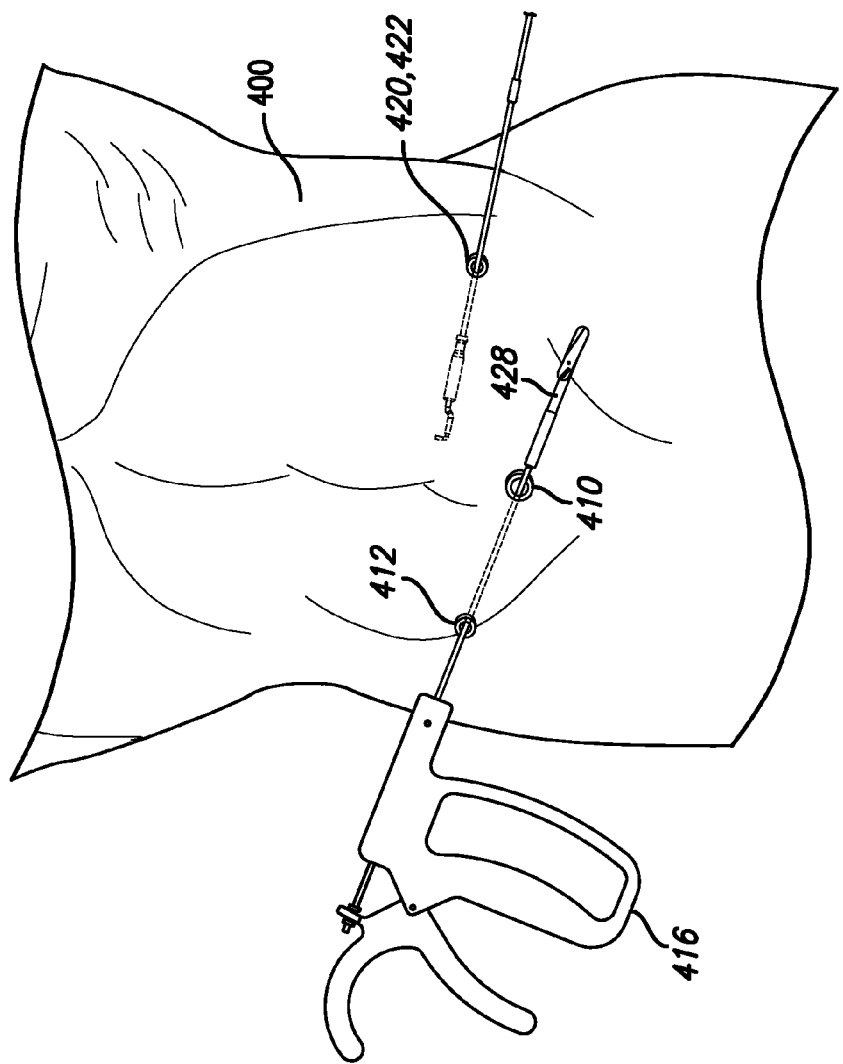
Figure 31:
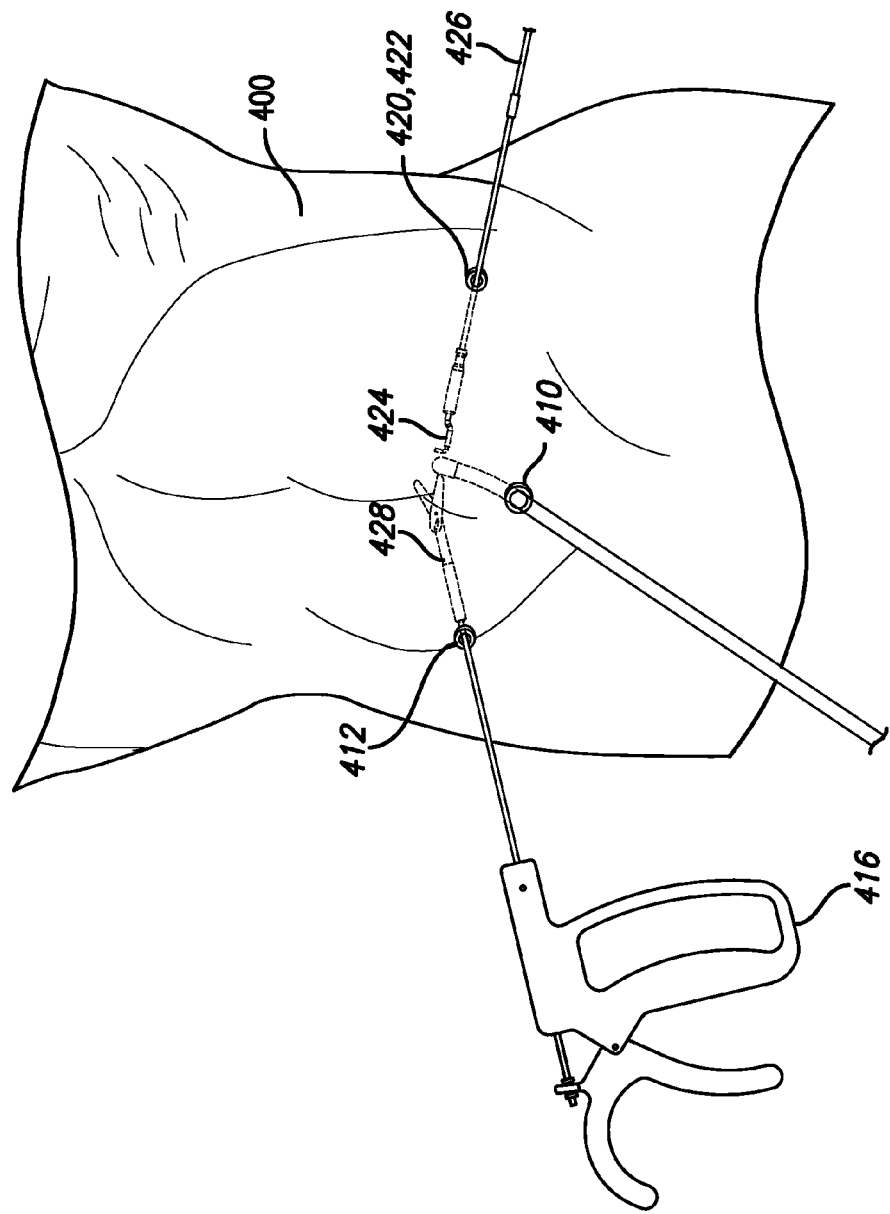

Next, the method further comprises passing the first part of the first device and second part of the first device from the body cavity back through the first opening (and through the first port when present) and into the space outside of the body, uncoupling and removing the first part of the first device from the second part of the first device. In one embodiment, as can be seen in FIG. 29 through FIG. 31, the method further comprises passing the second part of the first device back through the first opening (and through the first port when present) and into the body cavity, and then back through the second opening (and through the second port when present) thereby removing the first part of the first device from the body. In another embodiment, the first part of the first device is a first, first part of the first device, and the method further comprises coupling a second, first part of the first device to the second part of the first device in the space outside of the body to make a second, first device, passing the second, first part of the first device coupled to the second part of the first device back into the body cavity through the first opening (and through the first port when present) and using the second, first device to perform a procedure within the body cavity. In one embodiment, the method further comprises repeating these steps using a third, first part of the first device in place of the second, first part of the first device, as will be understood by those with skill in the art with reference to this disclosure.

In one embodiment, the method comprises using a surgical robot to control one or more than one of the devices. In a preferred embodiment, the surgical robot is a da Vinci® robot available from Intuitive Surgical, Inc., Sunnyvale, Calif. US. In another preferred embodiment, the surgical robot is a surgical robot available from Hansen Medical, Mountain View, Calif. US. In another preferred embodiment, the surgical robot is an integrated endoscopic robotic EndoSAMURAI® available from Olympus Medical Systems Corporation, Center Valley, Pa. US.

Figure 32:
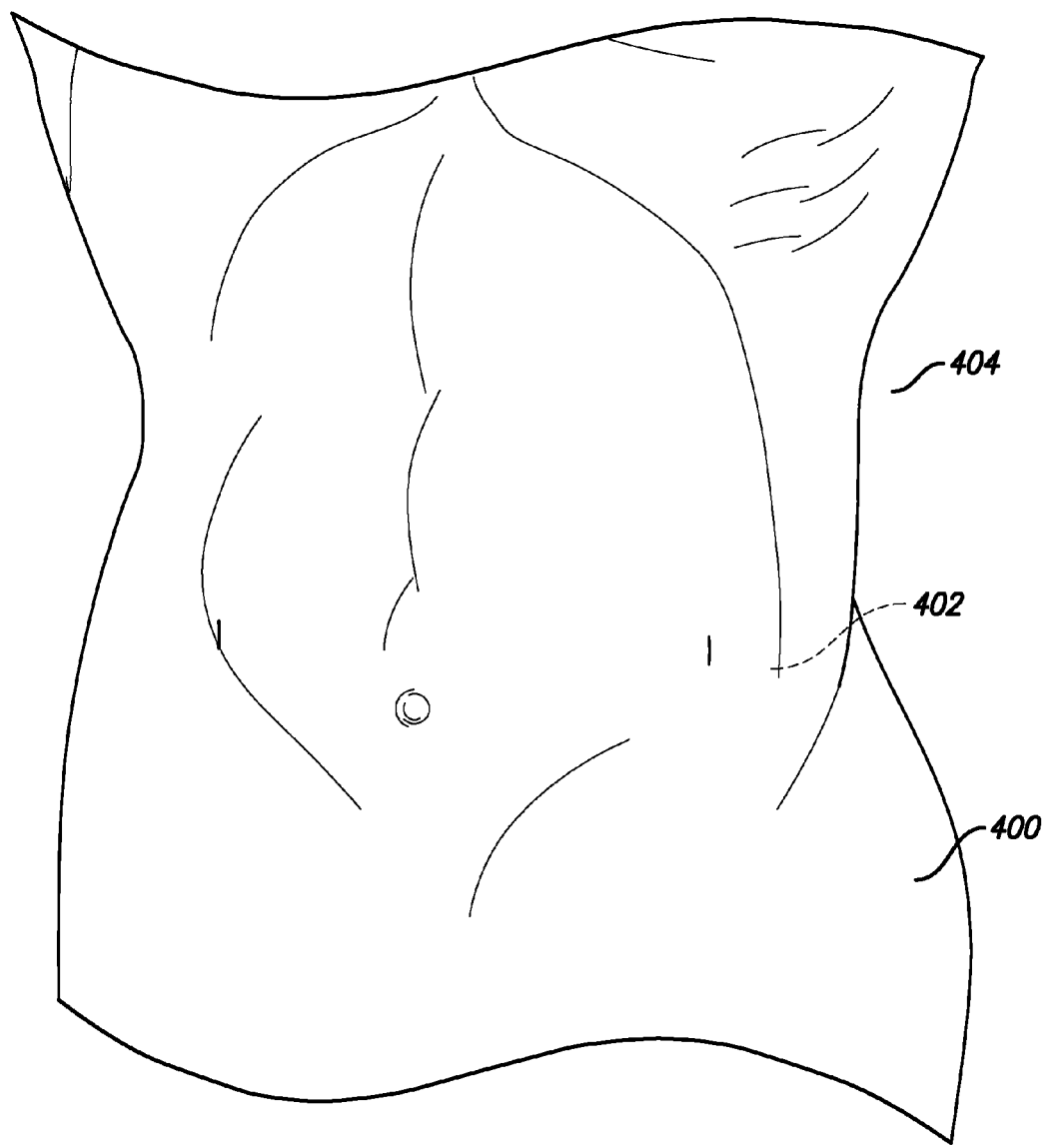

Finally, as can be seen in FIG. 32, the method further comprises removing all devices from within the body cavity and removing all ports, and closing any openings greater than 5 mm according to standard techniques, as will be understood by those with skill in the art with reference to this disclosure. Incisions 5 mm or less generally do not need to be closed but will seal themselves. Placement of the first opening in the umbilicus or umbilical crease allows the scar for the first opening to be essentially invisible after healing. Use of very small 3 mm or less incisions for the remaining openings allows the skin to heal essentially without any visible scaring after healing.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

What is claimed is:

1. A device for use in performing minimally invasive surgery, the device comprising a user interface comprising:
    a proximal portion, an intermediate portion and a distal portion, where the intermediate portion connects the proximal portion to the distal portion; and
    a pushrod, a shaft and a spring;
    where the distal portion is configured to reversibly mate with a working end;
    where the proximal portion is configured to allow a user to hold and direct the user interface, and to operate the working end attached to the distal portion of the user interface;
    where the proximal portion of the user interface comprises a proximal handle and a distal handle joined together by and rotatable around a pivot;
    where the pushrod comprises a proximal portion of the pushrod and a distal portion of the pushrod;
    where the proximal portion of the pushrod comprises a proximal end of the proximal portion of the pushrod, and comprises a distal end of the proximal portion of the pushrod;
    where the proximal end of the proximal portion of the pushrod is linked to the proximal handle, such that movement of the proximal handle around the pivot translates into axial movement of the pushrod;
    where the distal portion of the pushrod comprises a proximal end of the distal portion of the pushrod, and comprises a distal end of the distal portion of the pushrod;
    where the distal end of the proximal portion of the pushrod is joined to the proximal end of the distal portion of the pushrod at a junction;
    where the distal end of the distal portion of the pushrod comprises an expansion for mating with the working end, the working end comprising a head piece having a proximal portion of the head piece connected to a distal portion of the head piece;
    where the proximal portion of the head piece defines a recess for laterally receiving the expansion such that the proximal portion of the head piece mates with the distal portion of the shaft of the user interface and with the distal end of the working end pushrod;
    where the shaft comprises a hollow tubular structure comprising a longitudinal axis and further comprises a proximal portion of the shaft and a distal portion of the shaft;
    where the shaft surrounds at least part of the distal portion of the pushrod; where the distal portion of the pushrod is axially slidable within the shaft; and
    where the spring surrounds the proximal end of the distal portion of the pushrod, and the spring is between and abuts the distal end of the proximal portion of the pushrod and the proximal portion of the shaft.

2. The device of claim 1, where the user interface further comprises a shaft securing pin configured to insert within a recess in the distal handle, thereby securing the shaft from moving relative to the distal handle.

3. The device of claim 1, where the shaft comprises an outer transverse diameter and the outer transverse diameter is between 1 mm and 3 mm.

4. The device of claim 1, where the shaft comprises an outer transverse diameter and the outer transverse diameter is between 2 mm and 2.2 mm.

5. The device of claim 1, further comprising the working end for performing a function during minimally invasive surgery, where the working end is configured to reversibly mate with the distal end of the distal portion of the user interface.

6. The device of claim 5, where the function is selected from the group consisting of canulating, clip application, cutting, grasping, lighting, recording images, retracting, sealing, suctioning, and viewing images.

7. The device of claim 1, wherein the working end has a grasping function, the working end further comprising:
    a working end pushrod comprising a proximal portion of the working end pushrod and a distal end of the working end pushrod;
    a first jaw and a second jaw connected to the distal end of the working end pushrod by a jaw pivot; and
    a shaft clamp and one or more than one shaft clamp pins for aligning the shaft clamp with the proximal portion of the head piece;
    where the distal portion of the head piece is connected to the proximal portion of the working end pushrod by a jaw pin;
    where the first jaw and the second jaw approximate and separate from each other in response to axial movement of the working end pushrod; and
    where the distal portion of the shaft and the distal end of the working end pushrod are secured to the head piece by placing the shaft clamp onto the proximal portion of the head piece and securing the shaft clamp onto the proximal portion of the head piece by threading a threaded fastener over both the shaft clamp and the proximal portion of the head piece.

8. The device of claim 1, wherein the working end has a cutting function, the working end further comprising:
    a working end pushrod comprising a proximal portion of the working end pushrod and a distal end of the working end pushrod;
    a first blade and a second blade connected to the distal end of the working end pushrod by a blade pivot; and
    a shaft clamp and one or more than one shaft clamp pins for aligning the shaft clamp with the proximal portion of the head piece;
    where the distal portion of the head piece is connected to the proximal portion of the working end pushrod by a blade pin;

where the first blade and the second blade approximate and separate from each other in response to axial movement of the working end pushrod; and where the distal portion of the shaft and the distal end of the working end pushrod are secured to the head piece by placing the shaft clamp onto the proximal portion of the head piece and securing the shaft clamp onto the proximal portion of the head piece by threading a threaded fastener over both the shaft clamp and the proximal portion of the head piece.

9. A device for use in performing minimally invasive surgery, the device comprising a working end for mating with a user interface, the working end having a grasping function, and the working end further comprising:

a head piece comprising a proximal portion of the head piece connected to a distal portion of the head piece;

a working end pushrod comprising a proximal portion of the working end pushrod and a distal end of the working end pushrod;

a first jaw and a second jaw connected to the distal end of the working end pushrod by a jaw pivot; and a shaft clamp and one or more than one shaft clamp pins for aligning the shaft clamp with the proximal portion of the head piece;

where the distal portion of the head piece is connected to the proximal portion of the working end pushrod by a jaw pin;

where the first jaw and the second jaw approximate and separate from each other in response to axial movement of the working end pushrod;

where the proximal portion of the head piece comprises a recess for mating with the distal portion of a shaft of the user interface and the distal end of the working end pushrod; and where the distal portion of the shaft and the distal end of the working end pushrod are secured to the head piece by placing the shaft clamp onto the proximal portion of the head piece and securing the shaft clamp onto the proximal portion of the head piece by threading a threaded fastener over both the shaft clamp and the proximal portion of the head piece.

10. A device for use in performing minimally invasive surgery, the device comprising a working end for mating with a user interface, the working end having a cutting function, and the working end further comprising:

a head piece comprising a proximal portion of the head piece connected to a distal portion of the head piece;

a working end pushrod comprising a proximal portion of the working end pushrod and a distal end of the working end pushrod;

a first blade and a second blade connected to the distal end of the working end pushrod by a blade pivot; and a shaft clamp and one or more than one shaft clamp pins for aligning the shaft clamp with the proximal portion of the head piece;

where the distal portion of the head piece is connected to the proximal portion of the working end pushrod by a blade pin;

where the first blade and the second blade approximate and separate from each other in response to axial movement of the working end pushrod;

where the proximal portion of the head piece comprises a recess for mating with the distal portion of a shaft of the user interface and the distal end of the working end pushrod; and where the distal portion of the shaft and the distal end of the working end pushrod are secured to the head piece by placing the shaft clamp onto the proximal portion of the head piece and securing the shaft clamp onto the proximal portion of the head piece by threading a threaded fastener over both the shaft clamp and the proximal portion of the head piece.

\* \* \* \* \*